United States Patent [19]

Mizumoto et al.

[11] Patent Number: 5,629,198
[45] Date of Patent: May 13, 1997

[54] ANTI-HIV AGENT

[75] Inventors: Kenji Mizumoto; Hiroshi Tsuboi; Hideki Miyajima; Hiroshi Fujimoto; Katsumi Ajisaka; Yukio Fujiki; Hajime Tsunoo, all of Odawara, Japan

[73] Assignee: Meiji Milk Products Co., Ltd., Tokyo, Japan

[21] Appl. No.: 175,438

[22] PCT Filed: Jul. 31, 1992

[86] PCT No.: PCT/JP92/00977

§ 371 Date: Jan. 12, 1994

§ 102(e) Date: Jan. 12, 1994

[87] PCT Pub. No.: WO93/03035

PCT Pub. Date: Feb. 18, 1993

[30] Foreign Application Priority Data

Aug. 2, 1991 [JP] Japan ................................. 3-194452
Mar. 19, 1992 [JP] Japan ................................. 4-063492

[51] Int. Cl.$^6$ .................... A61K 39/00; G01N 33/564; G01N 33/53; C07K 1/00
[52] U.S. Cl. ................... 435/262; 435/974; 435/975; 435/268; 435/269; 530/402; 530/333; 424/184.1; 424/188.1; 424/201.1; 424/148.1; 424/520; 424/530; 514/410
[58] Field of Search ............... 424/184.1, 188.1, 424/201.1, 148.1, 520, 530; 514/410; 530/402, 333; 435/974, 975, 262, 268, 269

[56] References Cited

U.S. PATENT DOCUMENTS

| | | | |
|---|---|---|---|
| 4,883,790 | 11/1989 | Levy et al. | 540/145 |
| 5,164,486 | 11/1992 | Tsunoo et al. | 424/85.8 |
| 5,192,788 | 3/1993 | Dixon et al. | 514/410 |
| 5,256,412 | 10/1993 | Tsunoo et al. | 424/85.8 |

FOREIGN PATENT DOCUMENTS

| | | | |
|---|---|---|---|
| 0267038 | 5/1988 | European Pat. Off. | A07K 3/08 |
| 0276121 | 7/1988 | European Pat. Off. | A61K 39/395 |
| 0337598 | 10/1989 | European Pat. Off. | A61K 31/40 |

OTHER PUBLICATIONS

Takami et al. 1992. Maleylated human serum albumin inhibits Hiv-1 . . . BBA. 1180:180–186.
Muller–Eberhard et al. 1989. Transport of Tetrapyrroles by proteins. Seminars in Hematology 26(2):86–104.
Dixon et al. 1992. Amino–and hydrox tetraphenylporphyrins with activity . . . Antiviral Chem. & Chemotherap. 3(5):279–82.
Ding et al. 1992. Anti–human immunodeficiency virus effects . . . Biochem. Pharmocol. 44(8):1675–79.
Levere et al. 1991. Heme inhibits human imnumo deficiency virus . . . PNAS. 88:1756–59.
DeCamp. et al. 1992 Specific Inhibition of HIV–1 Protease by Boronated Porphyrins. J. Med. Chem. 35:3426–28.
Sandstrom et al. 1987. Antiviral Therapyin AIDS Clinical Pharmalogical Properties . . . Drugs 34:372–390.
Fox 1994. No winners against AIDS. Bio/Technology 12:128.
Haynes. 1993. Scientific and Social Issues of Human Immunodeficiency . . . Science 260:1279–86.

*Primary Examiner*—James C. Housel
*Assistant Examiner*—N. M. Minnifield
*Attorney, Agent, or Firm*—Bacon & Thomas

[57] ABSTRACT

The invention relates to an anti-HIV agent comprising, as an active ingredient, at least one porphyrin derivative selected from the following derivatives (A) and (B):

(A) porphyrins modified with a compound selected from carbodiimides, alkylenediamines and alcohols; and (B) complexes of a plasma protein or a chemically modified plasma protein and a porphyrin which may have been modified with a compound selected from carbodiimides, alkylenediamines and alcohols.

This anti-HIV agent is excellent in killing effect on HIV-infected cells, inhibitory effect on cytopathy due to HIV infection and HIV-replication inhibiting effect, and high in safety.

26 Claims, 30 Drawing Sheets

Before staining 400nm
(Absorption attributable to PP)

After staining
(Absorption attributable to protein)

A : S-HSA-PP
C : S-HSA-EDC-PP(A)
E : S-HSA
G : EDC-PP(A)+(B)

B : S-HSA-EDC-PP
D : S-HSA-EDC-PP(B)
F : HSA

ANTI-HIV AGENT

TECHNICAL FIELD

The present invention relates to a novel anti-HIV (Human Immunodeficiency Virus) agent.

BACKGROUND ART

Since 1983, it has been explicated that HIV forms the cause of AIDS (Acquired Immune Deficiency Syndrome) and AIDS-related diseases. At the beginning of its discovery, HIV had been differently named LAV (Lymphoadenopathy Associated Virus) by French researchers, or HTLV-III (Human T-lymphotropic Virus Type III) or ARV (AIDS-Related Virus) by American researchers. However, it was determined in 1986 that the designation of the virus is unified into HIV. WHO predicts that AIDS patients and HIV-infected persons in the world will reach ten millions and forty millions, respectively, by 2000. On the other hand, AIDS patients and HIV-infected persons in Japan are 378 and 1,656, respectively, as of April, 1991, and are increasing surely.

As described above, AIDS now grows into a great foe of the human. However, no basic therapy has been found yet. Only azidothymidine (AZT; 3'-azido-3'-deoxythymidine) has been approved up to the present [Mitsuya, et al.: Proc. Natl. Acad. Sci. U.S.A. 82, 7096–7100 (1985)]. AZT has been confirmed in its effectiveness by what life-prolonging effect is recognized to a significant extent, and so on. On the other hand, it has been said that a myelodepresant effect is remarkably observed as a side effect in addition to headache and gastrointestinal disorders, and long-term administration hence offers a problem [Richmann, D. D. et al.: New Engl. J. Med., 317, 185–197 (1987)]. AZT has also been said that it is of no effect on cells already infected with HIV, and although it can prevent the crisis of AIDS-related complex, it is directly useless for remedy after infection.

In addition to AZT, many anti-HIV agents including nucleic acid derivatives, soluble CD4 and the like have been researched and developed. As literature related to the present invention, there are documents which describe porphyrin or chemically modified plasma proteins as having an anti-HIV activity.

Asanaka et al. have reported that protoporphyrin exhibits an anti-HIV activity in an MT-4/LAV-infected system [AIDS 3, 403–404 (1989)]. However, this mechanism is considered to be the same as the anti-HIV effect of dextran sulfate in which so-called adsorption stage of HIV on MT-4 cells is inhibited.

Levere et al. have proved with human peripheral blood lymphocytes and H9 cells that when AZT and heme are used in combination in an amount of 1–10 μM against AZT-resistant HIV, the replication of HIV can be remarkably inhibited [Proc. Natl. Acad. Sci. U.S.A., 88, 1756–1759 (1991)].

Tsunoo et al. have proved that succinylated or maleylated plasma proteins have an anti-HIV activity (Japanese Patent Application Laid-Open No. 275824/1990).

All the anti-HIV activities of the substances described above are against the infection and proliferation of HIV, and have no killing effect on cells persistently infected with HIV.

It is accordingly an object to provide an anti-HIV agent which has a killing effect on HIV-infected cells and is useful for the prophylaxis and treatment of AIDS.

Thus, the present inventors have synthesized a number of chemically modified porphyrins and screened them from both standpoints of the killing effect on cells persistently infected with HIV and the safety for normal cells. As a result, it has been found that a porphyrin derivative obtained by modifying a porphyrin with a carbodiimide, an alkylenediamine or an alcohol, or a complex of a porphyrin or the porphyrin derivative with a plasma protein or a chemically modified plasma protein is excellent in killing effect on the cells persistently infected with HIV and high in safety for the normal cells, thus leading to completion of the present invention.

DISCLOSURE OF THE INVENTION

According to the present invention, there is provided an anti-HIV agent comprising, as an active ingredient, at least one porphyrin derivative selected from the following derivatives (A) and (B):

(A) porphyrins modified with a compound selected from carbodiimides, alkylenediamines and alcohols; and (B) complexes of a plasma protein or a chemically modified plasma protein and a porphyrin which may have been modified with a compound selected from carbodiimides, alkylenediamines and alcohols.

Among these porphyrin derivatives, the following derivatives (A') and (B') are novel compounds not yet described in literature. According to the present invention, there are thus provided the following porphyrin derivatives (A') and (B'):

(A') porphyrins modified with a carbodiimide or an alkylenediamine; and (B') complexes of a plasma protein or a chemically modified plasma protein and a porphyrin which may have been modified with a carbodiimide or an alkylenediamine (excluding complexes of a plasma protein and an unmodified porphyrin).

BRIEF DESCRIPTION OF THE DRAWINGS

FIG. 31 illustrates weight changes in a toxicity test of EDC-Hemin and S-HSA-EDC-Hemin to mice as the days roll on.

BEST MODE FOR CARRYING OUT THE INVENTION

Figure 1:
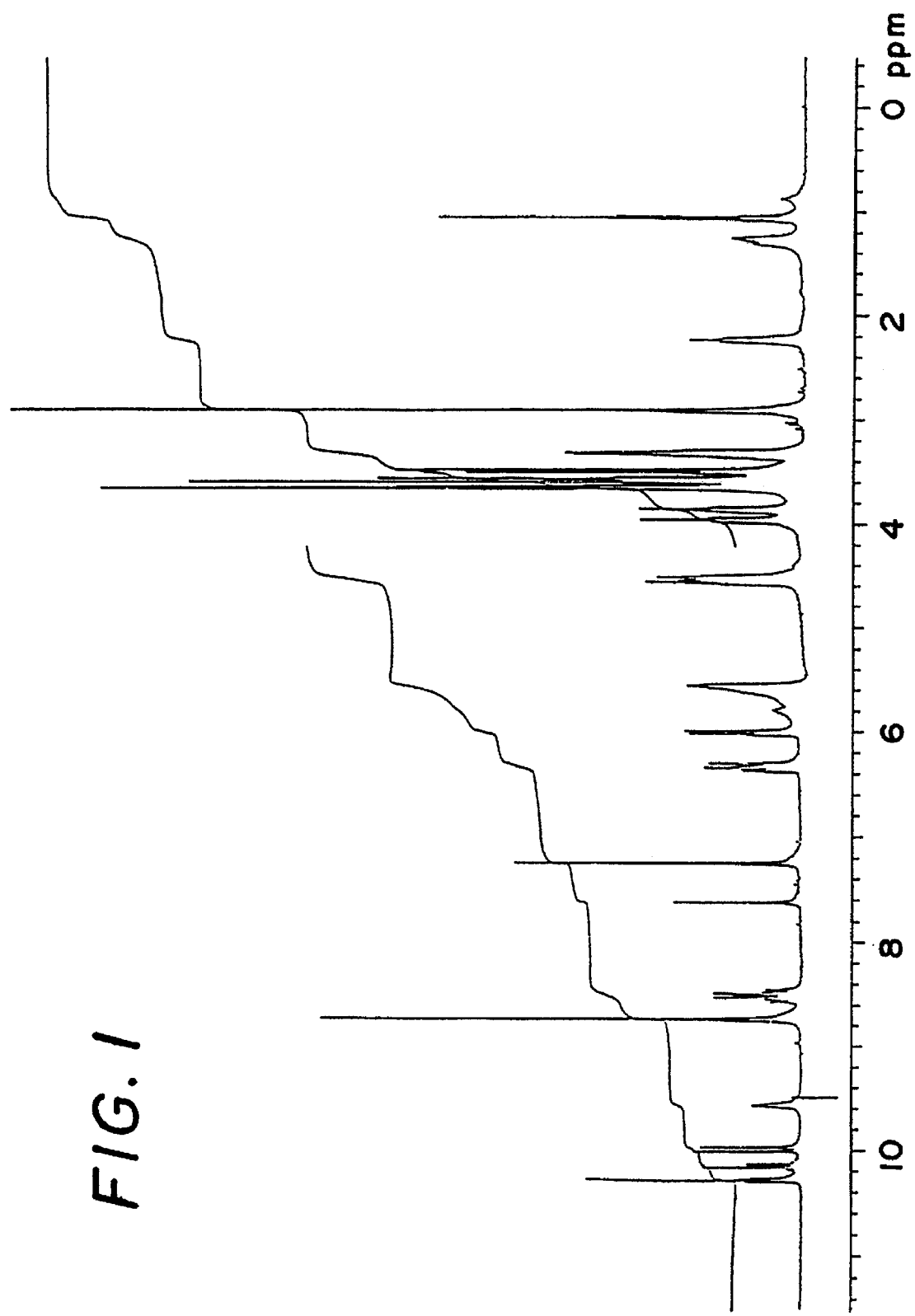
FIG. 1 illustrates a one-dimensional $^1$H-NMR of EDC-Hemin.
Figure 2:
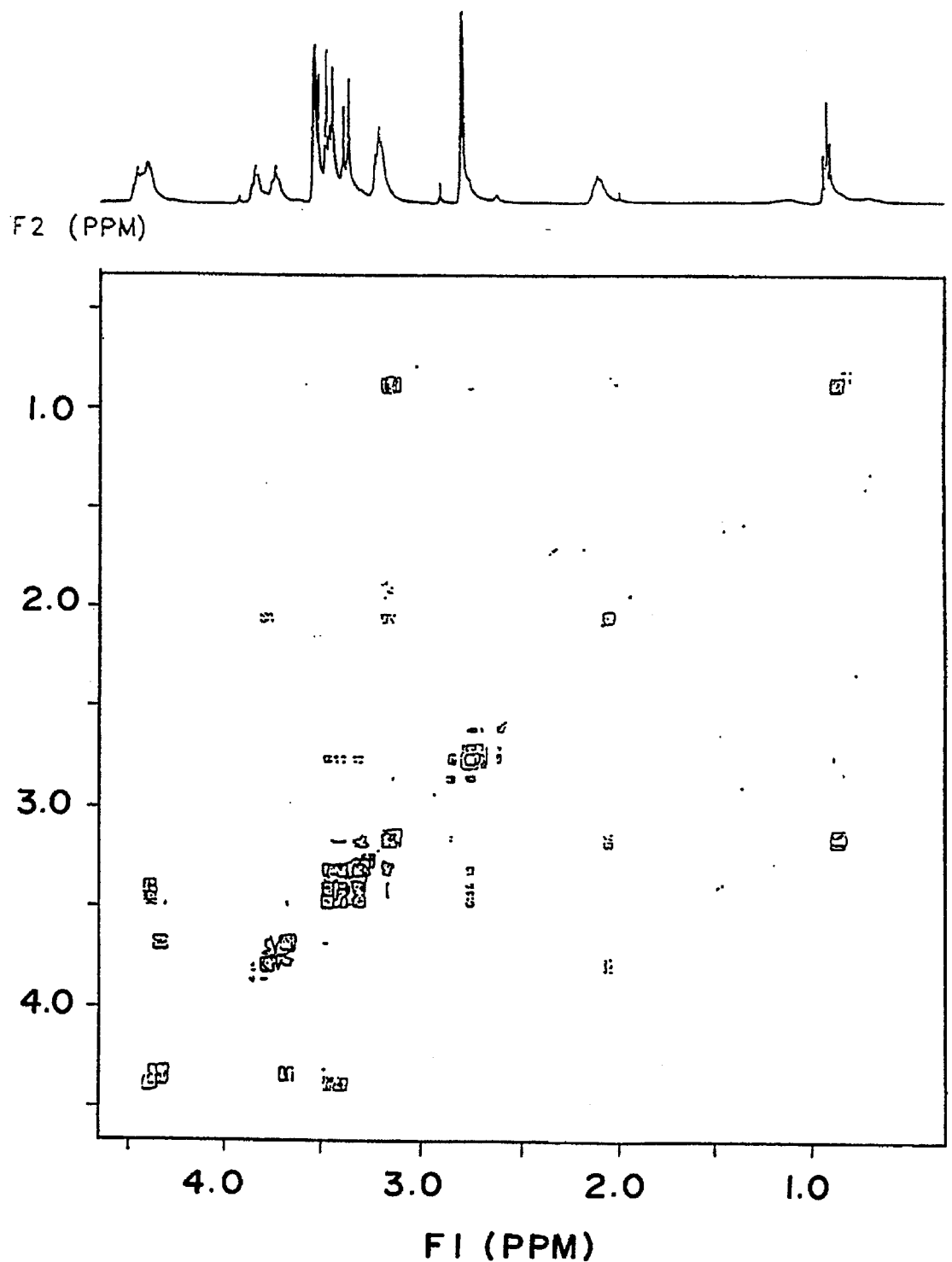
FIG. 2 illustrates a two-dimensional NMR (H-H COSY spectrum) of EDC-Hemin.
Figure 3:
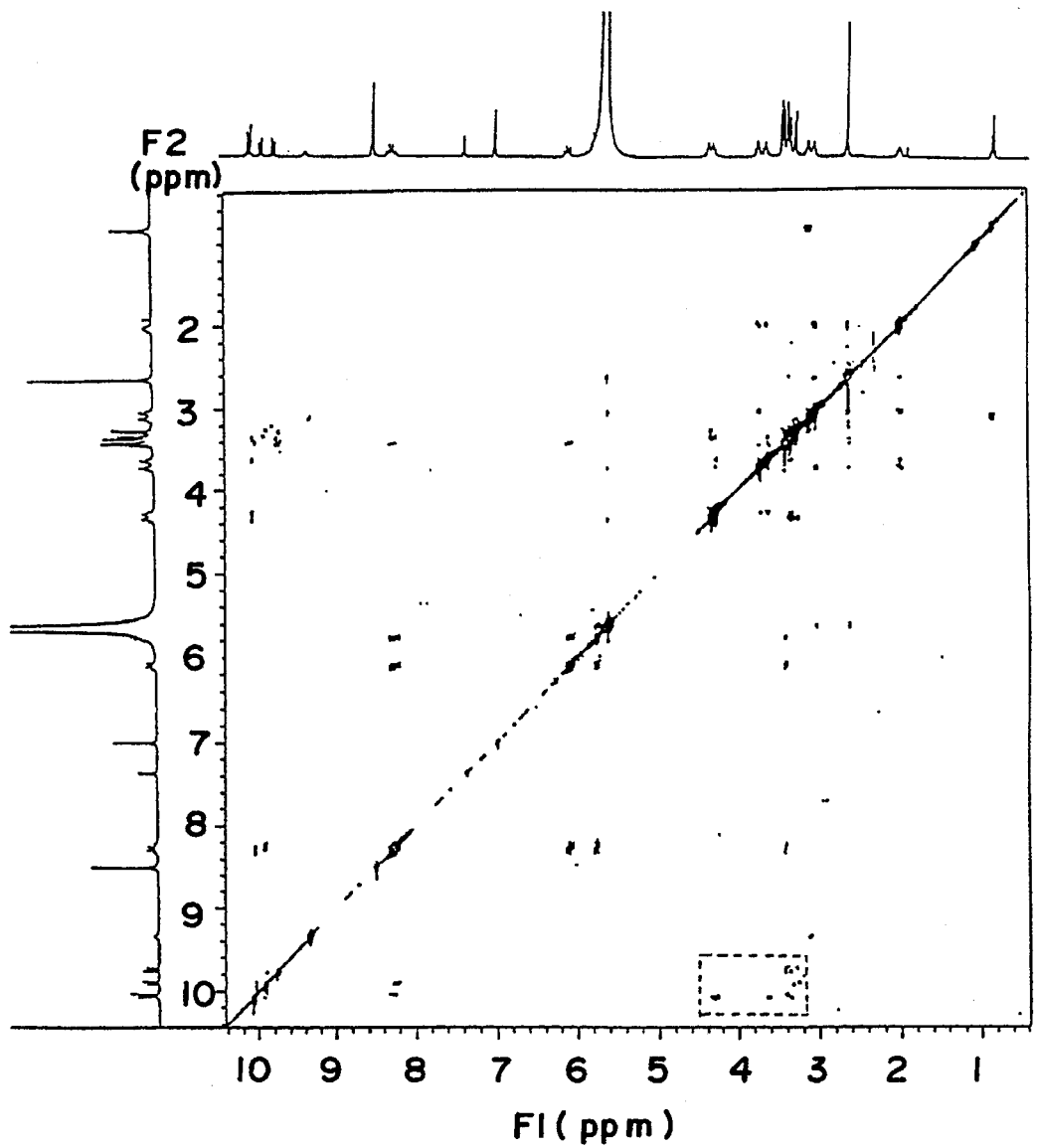
FIG. 3 illustrates a two-dimensional NMR (H-H ROESY spectrum) of EDC-Hemin.
Figure 4:
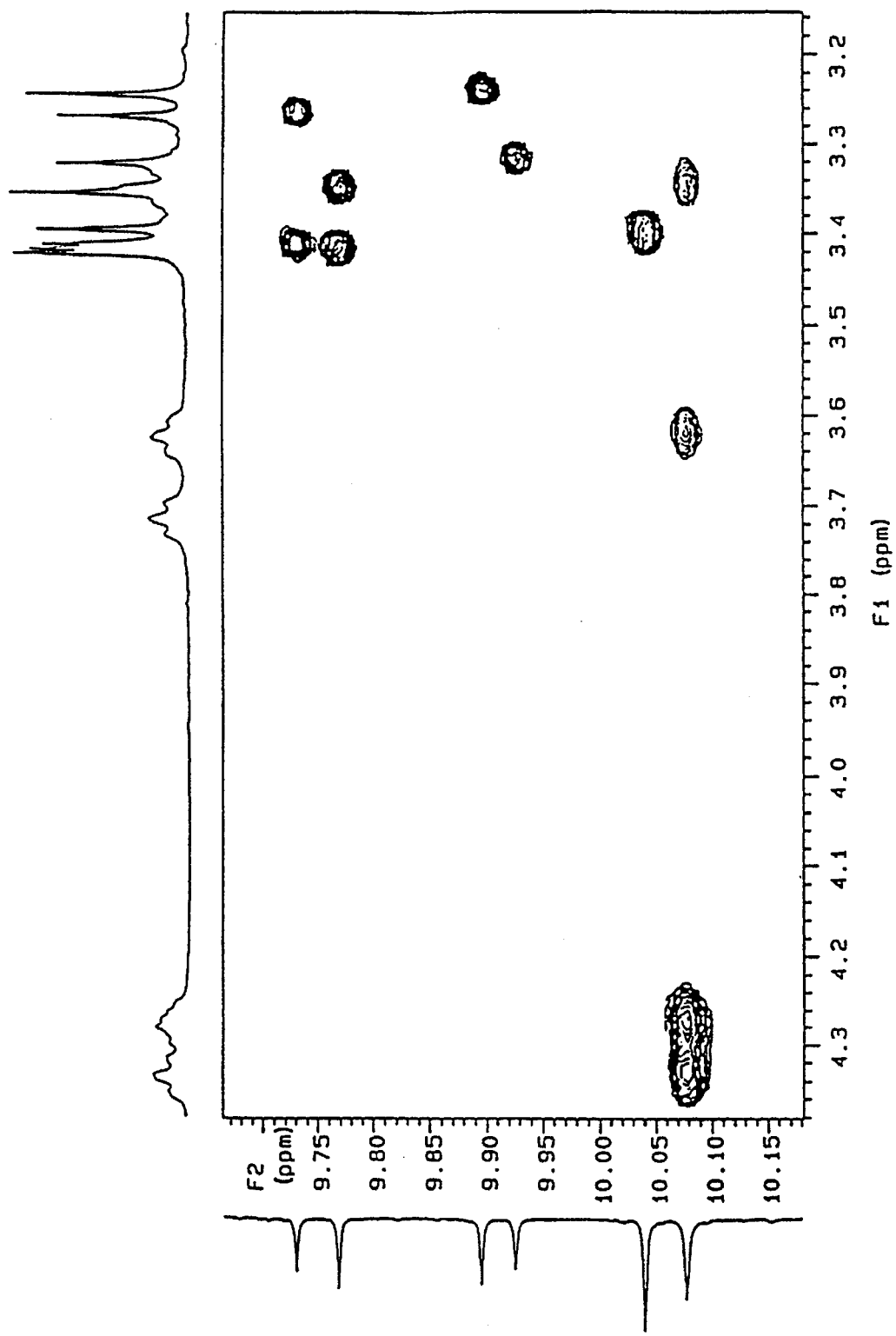
FIG. 4 is an enlarged view of a portion surrounded by a broken line in FIG. 3.

The porphyrins (A) modified with a compound selected from carbodiimides, alkylenediamines and alcohols (hereinafter abbreviated as "porphyrin derivatives (A)"), which are active ingredients in the anti-HIV agents according to the present invention, are prepared by reacting a carbodiimide, alkylenediamine or alcohol with a porphyrin.

Porphyrin is a compound with a structure that four pyrrole rings (A–D) are joined to one another by methine groups: —CH═ (5,10,15,20), to form a ring. At least one of its side chains (2, 3, 7, 8, 12, 13, 17, 18) is substituted by a group such as methyl, ethyl, vinyl or carboxyethyl, thereby forming various kinds of porphyrins. Porphyrin is characterized in that various metal ions are separately bonded to a nitrogen atom of a pyrrole ring to form metalloporphyrins.

The porphyrins useful in the practice of this invention include metalloporphyrins and have at least one carboxyl group on its side chain. Of these, those having at least one carboxyethyl group, and particularly, having carboxyethyl groups at 13 and 17 positions are preferred. Specific examples thereof may include porphyrins and metalloporphyrins such as hemin (may called protoheme), protophorphyrin, mesoporphyrin, iron mesoporphyrin, hematoporphyrin, iron hematoporphyrin and deuteroporphyrin, and their physiological salts such as sodium salts and hydrochlorides. Besides, as a porphyrin having 3 carboxyl groups, may be mentioned sodium copper chlorophyllin.

On the other hand, no particular limitation is imposed on the carbodiimides so long as they have a carbodiimide structure (—N═C═N—). However, those represented by the following general formula (1) are preferred.

$$R^1—N═C═R^2 \quad (1)$$

wherein $R^1$ and $R^2$ mean individually a linear, branched or cyclic alkyl, dialkylaminoalkyl, or morpholinoalkyl group.

Examples thereof may include N,N'-dicyclohexylcarbodiimide (DCC), 1-ethyl-3-(3-dimethylaminopropyl)carbodiimide (EDC), 1-cyclohexyl-3-(3-dimethylaminopropyl)carbodiimide (CDC), 1-isopropyl-3-(3-dimethylaminopropyl)carbodiimide (IDC), 1-cyclohexyl-3-(2-morpholinoethyl)carbodiimide (CMC) and the like.

Examples of the alkylenediamines may include those represented by the following general formula (2):

$$\begin{array}{c} R^3 \\ \diagdown \\ R^4 \end{array} N—(CH_2)_m—\underset{R^5}{\underset{|}{CH}}—N \begin{array}{c} R^6 \\ \diagup \\ R^7 \end{array} \quad (2)$$

wherein $R^3$, $R^4$, $R^6$ and $R^7$ mean individually a hydrogen atom or an alkyl group, $R^5$ denotes a hydrogen atom, an alkyl group or a group represented by —CO—X—$R^8$ (in which X means an oxygen atom or NH, and $R^8$ denotes a hydrogen atom, a chain or cyclic alkyl group, or a benzyl group), and m stands for a number of 1–8.

No particular limitation is imposed on the alcohols so long as they are alcohols having 1–6 hydroxyl groups. Polyalkylene glycols or monoalkyl ethers thereof are particularly preferred. Specific examples thereof may include polyethylene glycols and polypropylene glycols having an average molecular weight of 400–100,000 or monomethyl ethers thereof, and the like.

The reaction of a porphyrin and a carbodiimide is conducted, for example, by using the carbodiimide in a proportion of 1–10 moles per mole of the porphyrin in an organic solvent or an aqueous alkali solution and stirring them for several tens minutes to several days at a temperature ranging from room temperature to 60° C. As the organic solvent, may be used pyridine, N,N-dimethylformamide, dimethylsulfoxide or the like, while a solution of NaOH or borate (for example, sodium tetraborate) may be used as the aqueous alkali solution. If the pH of the reaction mixture is in an acid range, the complex of the porphyrin and the carbodiimide is activated, so that it is hydrolyzed into a urea derivative originated in the carbodiimide and the original porphyrin. Therefore, the pH may preferably be within a range of 7–10.

With respect to the reaction of a porphyrin and an alkylenediamine or alcohol, it is only necessary to conduct the reaction under usual conditions for ester synthesis or amide synthesis. For example, the reaction is required only to use a carbodiimide such as DCC or EDC as a condensation agent in an organic solvent such as dimethylformamide and to stir at room temperature for several tens minutes to several tens hours.

After completion of the reaction, the reaction mixture is dialyzed to distilled water or a dilute buffer solution through a semipermeable membrane, thereby removing urea derivatives as by-products, and unreacted carbodiimide, alkylenediamine or alcohol.

After the dialysis, the contents may be subjected to liquid chromatography or liquid-liquid chromatography to conduct purification and separation. However, centrifugal partition chromatography (CPC) in which centrifugal force is applied to facilitate liquid-liquid two-phase separation is often used in pretreatment for the purification and collection of samples on an industrial scale, and may suitably be used in the practice of this invention.

As a solvent system upon subjecting to CPC, a water-chloroform system or water-butanol system is used to collect fractions in which absorption at 400 nm is observed. The thus-collected fractions are then concentrated. The number of revolutions of a rotor for CPC is suitably 100–1700 rpm. Incidentally, when the contents after the dialysis are lyophilized to remove water contained therein, the load in the subsequent chromatography is lightened.

The porphyrin derivative (A) thus obtained is an N-acylurea converted by the intramolecular rearrangement of an active ester type intermediate, or O-acylisourea, which has been formed by the reaction of the carboxyl group contained in the porphyrin as a starting material with the carbodiimide, or a product with the carboxyl group bonded by an amide linkage or an ester linkage to the amino group in the alkylenediamine or the hydroxyl group in the alcohol. In the porphyrin derivatives (A), there are various structural isomers for such reasons that the porphyrin as the starting material has a plurality of carboxyl groups and the carbodiimide has two reaction sites. In this invention, however, these isomers and mixtures thereof all may be used. In the porphyrin derivatives (A), there are also rotational isomers about the amide linkage. However, these isomers and mixtures thereof all may also be used in the present invention.

Specific examples of such porphyrin derivatives (A) may include a compound with one EDC molecule bonded to hemin (abbreviated as "EDC-Hemin), a compound with two EDC molecules bonded to hemin (abbreviated as "2EDC-Hemin"), a compound one CDC molecule bonded to hemin (abbreviated as "CDC-Hemin"), a compound with two CDC molecules bonded to hemin (abbreviated as "2CDC-Hemin"), a compound with one IDC molecule bonded to hemin (abbreviated as "IDC-Hemin"), a compound with two IDC molecules bonded to hemin (abbreviated as "2IDC-Hemin"), a compound with one N,N-dimethylethyldiamine molecule bonded to hemin (abbreviated as "DMEA-Hemin"), a compound with two DMEA molecules bonded to hemin (abbreviated as "2DMEA-Hemin"), a compound with one polyethylene glycol monomethyl ether molecule bonded to hemin (abbreviated as "PEG-Hemin"), a compound with one EDC molecule bonded to protoporphyrin (abbreviated as "EDC-PP), a compound with two EDC molecules bonded to protoporphyrin (abbreviated as "2EDC-PP"), a compound with one CDC molecule bonded to protoporphyrin (abbreviated as "CDC-PP"), a compound with two CDC molecules bonded to protoporphyrin (abbreviated as "2CDC-PP"), a compound with one IDC molecule bonded to protoporphyrin (abbreviated as "IDC-PP"), a compound with two IDC molecules bonded to protoporphyrin (abbreviated as "2IDC-PP"), a compound with one N,N-dimethylethyldiamine molecule bonded to protoporphyrin (abbreviated as "DMEA-PP"), a compound with one polyethylene glycol molecule bonded to protoporphyrin (abbreviated as "PEG-PP"), a compound with one EDC molecule bonded to iron mesoporphyrin (abbreviated as "EDC-Fe-MesoP), a compound with one IDC molecule bonded to iron mesoporphyrin (abbreviated as "IDC-Fe-MesoP), a compound with one EDC molecule bonded to iron hematoporphyrin (abbreviated as "EDC-Fe-HematoP), a compound with one IDC molecule bonded to iron hematoporphyrin (abbreviated as "IDC-Fe-HematoP), and the like.

Besides, the complexes (B) of a plasma protein or a chemically modified plasma protein and a porphyrin which may have been modified with a compound selected from carbodiimides, alkylenediamines and alcohols (hereinafter abbreviated as "porphyrin derivatives (B)"), which are another active ingredients in the anti-HIV agents according to the present invention, are prepared by reacting a plasma protein or a chemically modified plasma protein with a porphyrin or any one of the above-described porphyrin derivatives (A).

Here, the plasma protein may preferably be derived from the human or bovine. Human serum albumin (HSA), human immunoglobulin, human transferrin, human fibrinogen and bovine serum albumin are particularly preferred. On the other hand, the chemically modified plasma protein may preferably be obtained by the succinylation or maleylation of the plasma protein with succinic anhydride or maleic anhydride so as to make the polarity of a side chain after the chemical modification negative (−). By the way, the succinylated or maleylated plasma protein can be obtained in accordance with, for example, the process described in Japanese Patent Application Laid-Open No. 275824/1990. In this invention, succinylated human serum albumin and maleylated human serum albumin are abbreviated as "S-HSA" and "M-HSA", respectively.

The reaction of the porphyrin or the porphyrin derivative (A) with the plasma protein or the chemically modified plasma protein is conducted, for example, in the following manner. First, the porphyrin or the porphyrin derivative (A) is dissolved in an organic solvent, for example, dimethylsulfoxide (DMSO) or a 0.01N aqueous NaOH solution, at room temperature. An equivolume of distilled water is then added to the resultant solution to stir the mixture (Solution A). On the other hand, the plasma protein or the chemically modified plasma protein is dissolved in distilled water or a weakly alkaline solution (Solution B). The weight ratio of the porphyrin or the porphyrin derivative (A) to the plasma protein or the chemically modified plasma protein in the reaction is preferably 1:1–200, more preferably 1:5–180, most preferably 1:10–30.

Solution B is added to Solution A to react them for several hours at room temperature, and the reaction mixture is then neutralized with hydrochloric acid. The thus-treated reaction mixture is dialyzed to purified water (which is replaced several times) in an amount at least one hundred times the reaction mixture through a semipermeable membrane (molecular weight cut-off value: 12K–14K) for 2–3 days at room temperature. The dialyzate is then lyophilized to obtain the porphyrin derivative (B) according to the present invention.

Specific examples of the porphyrin derivatives (B) obtained in the above-described manner may include HSA- EDC-Hemin, Hemin, S-HSA-EDC-Hemin, S-HSA-2EDC-Hemin, S-HSA-CDC-Hemin(A), S-HSA-CDC-Hemin(B), S-HSA-2CDC-Hemin, S-HSA-IDC-Hemin, S-HSA-2IDC-Hemin, S-HSA-DMEA-Hemin, S-HSA-2DMEA-Hemin, S-HSA-PEG-Hemin, S-HSA-EDC-PP, S-HSA-2EDC-PP, S-HSA-CDC-PP, S-HSA-2CDC-PP, S-HSA-IDC-PP, S-HSA-2IDC-PP, S-HSA-DMEA-PP, S-HSA-PEG-PP, S-HSA-EDC-Fe-MesoP, S-HSA-IDC-Fe-MesoP, S-HSA-EDC-Fe-HematoP, S-HSA-Fe-HematoP, S-HSA-Hemin, S-HSA-PP, S-HSA-Fe-MesoP, S-HSA-Fe-HematoP, M-HSA-EDC-Hemin, M-HSA-CDC-Hemin, M-HSA-IDC-Hemin, M-HSA-EDC-PP, M-HSA-CDC-PP, M-HSA-IDC-PP, and the like.

Regarding the porphyrin derivatives (A) and (B), which are active ingredients in the anti-HIV agents according to the present invention, the following respects have been made clear from the results of various pharmaceutical tests and safety tests as described in the following examples.

(1) The porphyrin derivatives (A) and (B) have an extremely strong killing effect on various cells persistently infected with HIV, such as HIV-infected cells making use of MOLT-4 cells which are cancer cells derived from a leukosis patient. These porphyrin derivatives (A) and (B) are also recognized to have a killing effect on MT-4 cells belonging to a cell strain persistently infected with HTLV-1. Further, these porphyrin derivatives (A) and (B) strongly inhibit the cytopathy of HIV-infected MT-4 cells, which have a nature to be rapidly killed by the cytophathic effect when infected with HIV, at a low concentration. They also inhibit the production of a P24gag protein, which is an index to viral infection, by about 90%. Besides, their $TCID_{50}$ indicative of an actual viral infectious titer is equal or low compared with AZT. Furthermore, they not only inhibit infection, but also kill HIV-infected cells in the HIV-infected system making use of PBL nearer cells in vivo. At this time, no replication of HIV is entailed.

(2) On the other hand, it has been proved that the porphyrin derivatives (A) and (B) have little cytotoxic effect on PBL and fibroblast which are normal cells, and from the results of one-administration and repeated-administration toxicity tests making use of mice, the toxicity is extremely weak even in vivo.

(3) Incidentally, porphyrins such as hemin and protoporphyrin have a proliferation inhibiting effect on HIV, but show no killing effect on HIV-infected cells.

As described above, the anti-HIV agents according to the present invention have both strong inhibitory effect on the infection and proliferation of HIV and strong killing effect on cells persistently infected with HIV, and are extremely low in toxicity. Therefore, they are useful in prophylaxis of HIV infection and treatments for AIDS patients and AIDS-related complex (ARC).

Although the anti-HIV agents according to the present invention may be administered singly, they may be given as a drug preparation containing the present anti-HIV agent, at least one pharmaceutically permissible carrier and other remedies.

Their administration routes may include oral administration, intrarectal administration, topical administration and parenteral administrations (subcutaneous, intramuscular, intravenous and intradermal injections). In order to make the preparation a form suitable for its administration route, the compound according to the present invention may be mixed with the pharmaceutical carrier into the preparation. Examples of such a preparation may include capsules, tablets, grains or granules, emulsions, aqueous solutions, oily solutions, suspensions, suppositories, troches and the like. The preparation may be formulated using known carrier, antioxidant, isotonic agent, suspension stabilizer, buffer and/or bacteriostatic in accordance with the well-known conventional method.

The dose of the anti-HIV agent varies according to administration route, the age and condition of the patient to be dosed, and the like. However, the dose is generally 1 mg to 10 g per day for an adult. This amount of the anti-HIV agent is dosed once or in portions. In this case, the anti-HIV agent of this invention may be given together with any other anti-HIV agents.

EXAMPLES

The present invention will hereinafter be described by the following examples.

Preparation Example 1 (Synthesis of EDC-Hemin): (1) Synthesis of EDC-Hemin:

In 3 liters of 0.1M $Na_2B_4O_7$ (pH 9.6), were dissolved 30 g of hemin (product of Tokyo Kasei Kogyo Co., Ltd.) and 45 g of EDC (product of Dojindo Laboratories). The resultant solution was stirred for 30 minutes at room temperature by means of a magnetic stirrer. The reaction mixture was dialyzed to deionized water through a dialysis membrane (molecular weight cut-off: 12K–14K) produced by Spectrum Company for 2 days. The dialyzate was then lyophilized, thereby obtaining 36.52 g of dry powder. Incidentally, the dialysis may be conducted using holofibers or a tangential flow system.

This dry powder was subjected to CPC. More specifically, a solvent system composed of chloroform: methanol:water= 18:7:25 was thoroughly stirred with a separatory funnel to isolate an aqueous layer and a chloroform layer. Thereafter, the dry powder was dissolved in 216 ml of the chloroform layer and 144 ml of the aqueous layer. The resultant solutions were poured into a CPC column. CPC was conducted by using the aqueous layer and the chloroform layer as a stationary phase and a mobile phase, respectively. Elution was performed at a flow rate of 50 ml/min and the number of rotor revolutions of 400 rpm. The absorbance at 400 nm was monitored to fractionate the eluate into 3-liter portions. Fractions in which absorption was observed were collected to concentrate them under reduced pressure by a rotary evaporator, thereby obtaining 21.4 g of syrup.

The syrup was then dissolved in a solvent of Fraction No. 1 and subjected to chromatography on a silica gel column (2 kg) of 200 mm in diameter and 800 mm in length. The compositions of solvents were as follows:

| Fraction No. | 1 | 2 | 3 | 4 | 5 | 6 | 7 | 8 | 9 | 10 | 11 |
| --- | --- | --- | --- | --- | --- | --- | --- | --- | --- | --- | --- |
| Chloroform | 9 | 8 | 7 | 6 | 6 | 6 | 6 | 6 | 6 | 6 | 5 |
| Methanol | 1 | 2 | 3 | 4 | 4 | 4 | 4 | 4 | 4 | 4 | 5 |
| Acetic acid | 0.1 | 0.1 | 0.1 | 0.1 | 0.1 | 0.1 | 0.1 | 0.1 | 0.1 | 0.1 | 0.1 |

After silica gel was suspended in Solvent No. 1 to charge it into a column, the whole amount of the syrup was placed on the column. The eluate was collected in 10-liter portions. Each fraction was spotted by TLC (thin layer chromatography) and developed with a solvent system composed of chloroform:methanol:acetic acid=80:40:1. Fractions 6 to 8 were concentrated by a rotary evaporator to obtain 4.88 g of EDC-Hemin.

Alternatively, EDC-Hemin may be purified only by the chromatography on silica gel. More specifically, 20 g of the lyophilized reaction product were dissolved in the solvent of Fraction No. 1 and subjected to chromatography on a silica gel column (2 kg) of 200 mm in diameter and 800 mm in length. The compositions of solvents were adjusted as described below, thereby permitting the provision of EDC-Hemin without conducting the purification by CPC.

| Fraction No. | 1 | 2 | 3 | 4 | 5 | 6 | 7 | 8 |
|---|---|---|---|---|---|---|---|---|
| Chloroform | 9 | 8 | 7 | 6 | 6 | 6 | 6 | 6 |
| Methanol | 1 | 2 | 3 | 4 | 4 | 4 | 4 | 4 |
| Acetic acid | 0.1 | 0.1 | 0 | 0 | 0 | 0 | 0 | 0 |

Fractions 6 to 8 were concentrated by a rotary evaporator to obtain 3.3 g of EDC-Hemin.

Alternatively, EDC-Hemin may be purified only by CPC. More specifically, water-saturated n-butanol was charged as a stationary phase, and n-butanol-saturated aqueous ammonia (pH 10.5) was caused to flow as a mobile phase, thereby forming a two-layer system. The operation was performed at the number of rotor revolutions of 1200 rpm and a flow rate of 5 ml/min. A crude sample in an amount of 150 mg was dissolved in 10.5 ml of the stationary phase, and the solution was poured in the column. One liter of the mobile phase was caused to flow, and n-butanol-saturated aqueous acetic acid (pH 3.5) was then caused to flow further in an amount of 1 liter. Then, inversion elution was conducted. The eluate was collected in 2.5-ml portions, and Fractions 15–29 were concentrated by a rotary evaporator to obtain 12.6 mg of EDC-Hemin.

Further, as a modification of the purification by CPC only, there is the following method.

Water-saturated n-butanol was charged as a stationary phase, and (1) n-butanol-saturated aqueous ammonia (pH 10.5) was then charged as a mobile phase, thereby forming a two-layer system. The operation was performed at the number of rotor revolutions of 1700 rpm and a flow rate of 3 ml/min. After the crude sample after the dialysis was concentrated under reduced pressure by a rotary evaporator, 9 ml of the mobile phase (1) and 15 ml of the stationary phase were added to 6 ml of the concentrate (solids content: about 79 mg/ml). The mixture was stirred and then poured in the CPC column. About 380 ml of the mobile phase (1) were caused to flow, and about 630 ml of (2) n-butanol-saturated aqueous acetic acid (pH 3.5) as another mobile phase were then caused to flow, and about 380 ml of (3) n-butanol-saturated water as a further mobile phase were caused to flow. Thereafter, the stationary phase was caused to flow to conduct inversion elution. The eluate was collected in 3-ml portions, and Fractions 7–21 were concentrated by a rotary evaporator to obtain 56.6 mg of EDC-Hemin.

Another synthesis process of EDC-Hemin will hereinafter be described further.

In 2 liters of 0.1M $Na_2B_4O_7$ (pH 9.6), were dissolved 20 g of hemin (product of Tokyo Kasei Kogyo Co., Ltd.) and 30 g of EDC (product of Dojin Laboratories). The resultant solution was stirred for 30 minutes at 40° C. by means of a magnetic stirrer. The reaction mixture was cooled to 15° C., and then dialyzed to pyrogen-free water using a Tangential flow System making use of OMEGA MINISET (molecular weight cut-off: 5K, product of FILTRON Company). The dialyzate was then lyophilized, thereby obtaining about 20 g of dry powder. The powder was then dissolved in a solvent of Fraction No. 1 and subjected to chromatography on a silica gel column (2 kg) of 200 mm in diameter and 80 mm in length. The compositions of solvents were as follows:

| Fraction No. | 1 | 2 | 3 | 4 | 5 | 6 | 7 | 8 |
|---|---|---|---|---|---|---|---|---|
| Chloroform | 9 | 8 | 7 | 6 | 6 | 6 | 6 | 6 |
| Methanol | 1 | 2 | 3 | 4 | 4 | 4 | 4 | 4 |
| Acetic acid | 0.1 | 0.1 | 0.1 | 0 | 0 | 0 | 0 | 0 |

After silica gel was suspended in Solvent No. 1 to charge it into a column, the whole amount of the syrup was placed on the column. Each fraction was spotted by TLC and developed with a solvent system composed of chloroform:methanol:acetic acid=80:40:1. Fractions in which absorption was observed were concentrated by a rotary evaporator, thereby obtaining about 2 g of EDC-Hemin.

(2) Structure of EDC-Hemin:

$^1$H-NMR of EDC-Hemin was measured. After EDC-Hemin was dissolved in pyridine-$d_5$, a small amount of $SnCl_2$ was added to the solution to make iron in heme diamagnetic, thereby determining $^1$H-NMR at 400 MHz by an NMR apparatus, XL-400 or UNITY-400 manufactured by Varian Instruments Limited. TMS was used as an internal standard. The results are shown in FIGS. 1 to 4, in which FIG. 1 illustrates a one-dimensional spectrum of EDC-Hemin, FIG. 2 a COSY spectrum, FIG. 3 a ROESY spectrum, and FIG. 4 an enlarged spectrum of a portion surrounded by a broken line in FIG. 3. From the analysis of FIGS. 2–4, main signals in the EDC-Hemin spectrum shown in FIG. 1 were assigned as follows:

—$NHCH_2CH_3$
(3.14 ppm, 0.84 ppm)

—CO—N—$CH_2CH_2CH_2N(CH_3)_2$ (from the left, 3.75 ppm, 2.05 ppm, 3.13 ppm, 2.73 ppm)

⟩—$CH_2CH_2COOH$ (4.35 ppm, 3.43 ppm)

⟩—$CH_2CH_2CON$—

(4.33 ppm, 3.67 ppm)
Hemin Hα—Hδ
(10.10 ppm, 10.08 ppm, 9.75 and 9.80 ppm, 9.93 and 9.97 ppm)

EDC-Hemin was then methylated in the following manner. Namely, 14.4 mg of the EDC-Hemin derivative was dissolved in a mixed solvent composed of 9.2 ml of distilled water, 206 ml of 95% ethyl alcohol and 13.8 ml of 1M aqueous sodium bicarbonate solution, and the resultant solution was stirred at room temperature, to which trimethyloxonium tetrafluoroborate was added in amounts of 690 mg, 620 mg and 506 mg at intervals of 5 minutes, and the mixture was stirred. After 10 minutes, 1,200 ml of distilled water were added, and the methylated product was extracted with chloroform. The organic layer was concentrated, dried into solids, and then purified by chromatography on a silica gel column. A fraction eluted with a solvent system composed of chloroform:methyl alcohol:acetic acid=50:50:1 was concentrated to measure $^1$H-NMR. As a result, a signal corresponding to one methyl group originated from —$OCH_3$ was observed at 3.32 ppm.

Figure 5:
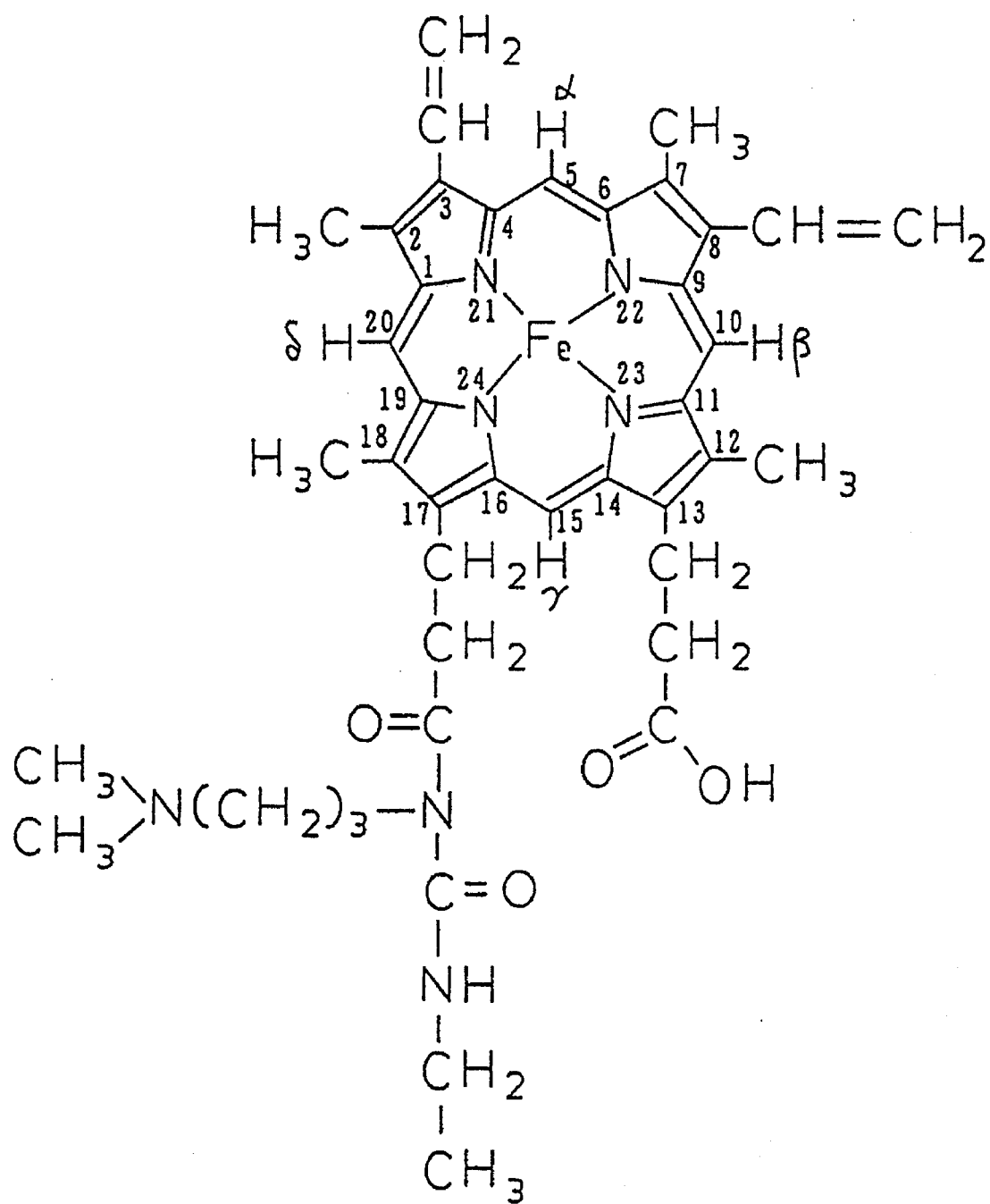
FIG. 5 illustrates an estimated chemical structural formula of EDC-Hemin.

From the above, the EDC-Hemin obtained above was determined to be a mixture of compounds in which the N,N-dimethylaminopropylamino moiety in EDC was bonded by an amide linkage to the carboxyl group of the carboxyethyl group at either 13- or 17-position of hemin. Of these compounds, EDC-Hemin of which the carboxyethyl group at the 17-position of hemin was modified is presumed to be a compound having a structure illustrated in FIG. 5. However, there is a rotational isomer about the amide linkage in this compound.

Preparation Example 2 (Synthesis of 2EDC-Hemin):
(1) Synthesis of 2EDC-Hemin:

In 180 ml of pyridine, were dissolved 5 g of hemin (product of Tokyo Kasei Kogyo Co., Ltd.) and 25 g of EDC (product of Dojin Laboratories). The resultant solution was stirred for 13 hours at 60° C. by means of a magnetic stirrer. After the reaction mixture was poured into 500 ml of water and stirred for 30 minutes, the formed product was extracted with chloroform. The extract was concentrated by a rotary evaporator.

One gram of this extract concentrate was subjected to CPC. More specifically, a solvent system composed of chloroform:methanol:acetic acid:water=360:140:6:500 was thoroughly stirred with a separatory funnel to isolate 1 ml of an aqueous layer and 1 ml of a chloroform layer, and a sample was dissolved to pour into a CPC column. CPC was conducted by using the chloroform layer as a mobile phase at a flow rate of 5 ml/min and the number of rotor revolutions of 500 rpm. The absorbance at 400 nm was monitored to collect the eluate in 10-ml portions. Fractions 41 to 60 in which absorption was observed were concentrated by a rotary evaporator, and dialyzed to water through a dialysis membrane (molecular weight cut-off value: 12K–14K) produced by Spectrum Company for 2 days. The dialyzate was then lyophilized to obtain 19.5 mg of 2EDC-Hemin.

Figure 6:
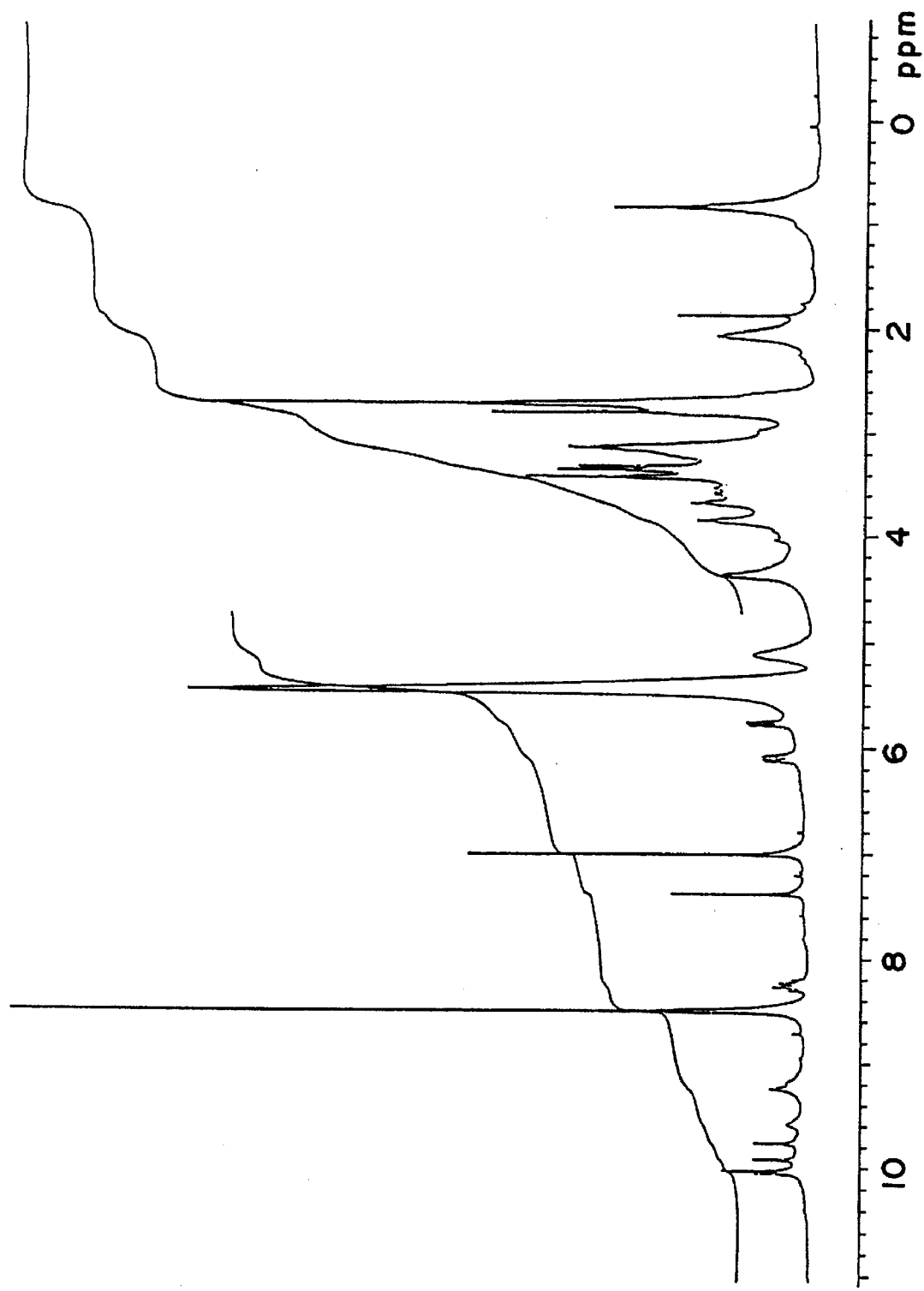
FIG. 6 illustrates a one-dimensional $^1$H-NMR of 2EDC-Hemin.
Figure 7:
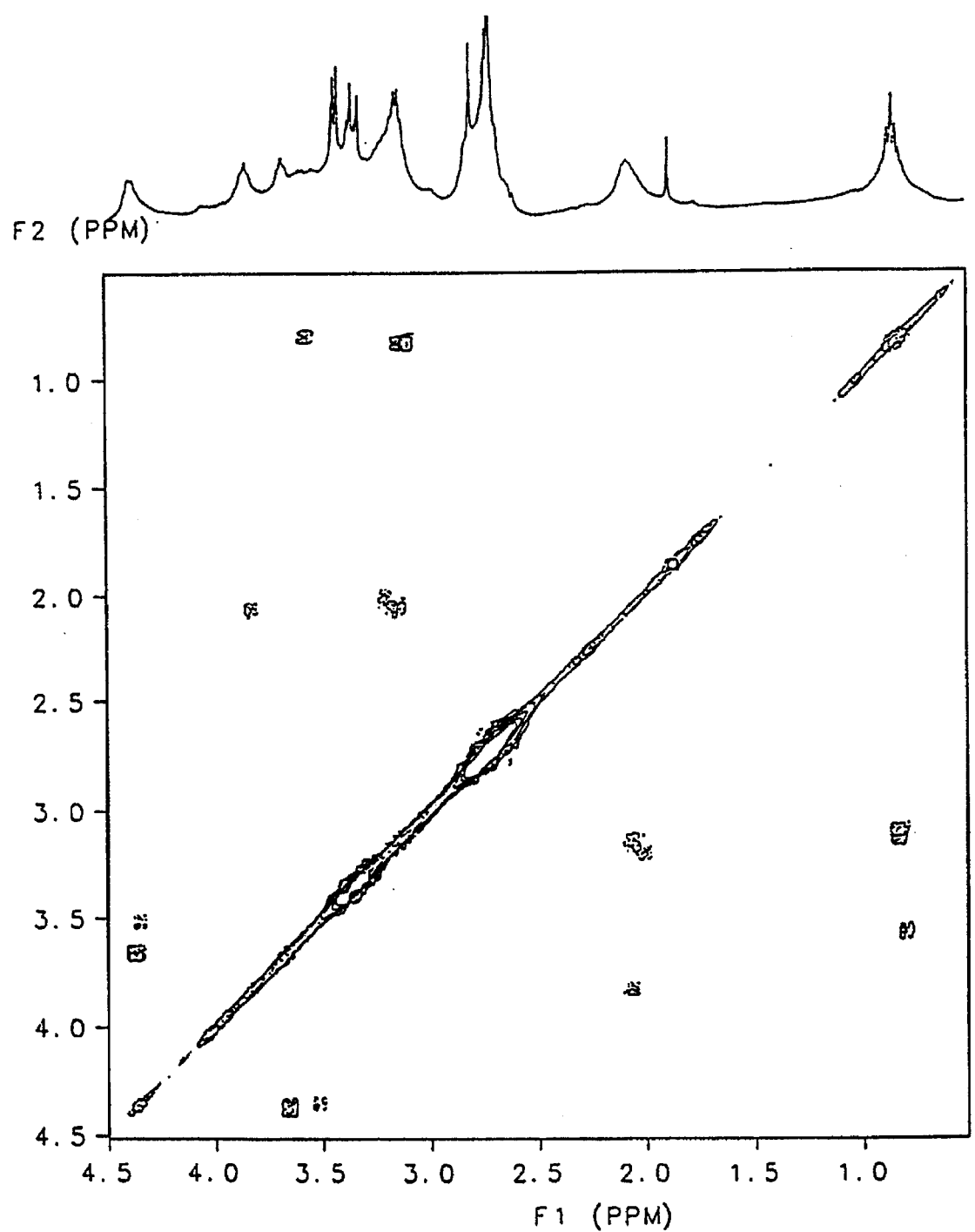
FIG. 7 illustrates a two-dimensional NMR (H-H COSY spectrum) of 2EDC-Hemin.
Figure 8:
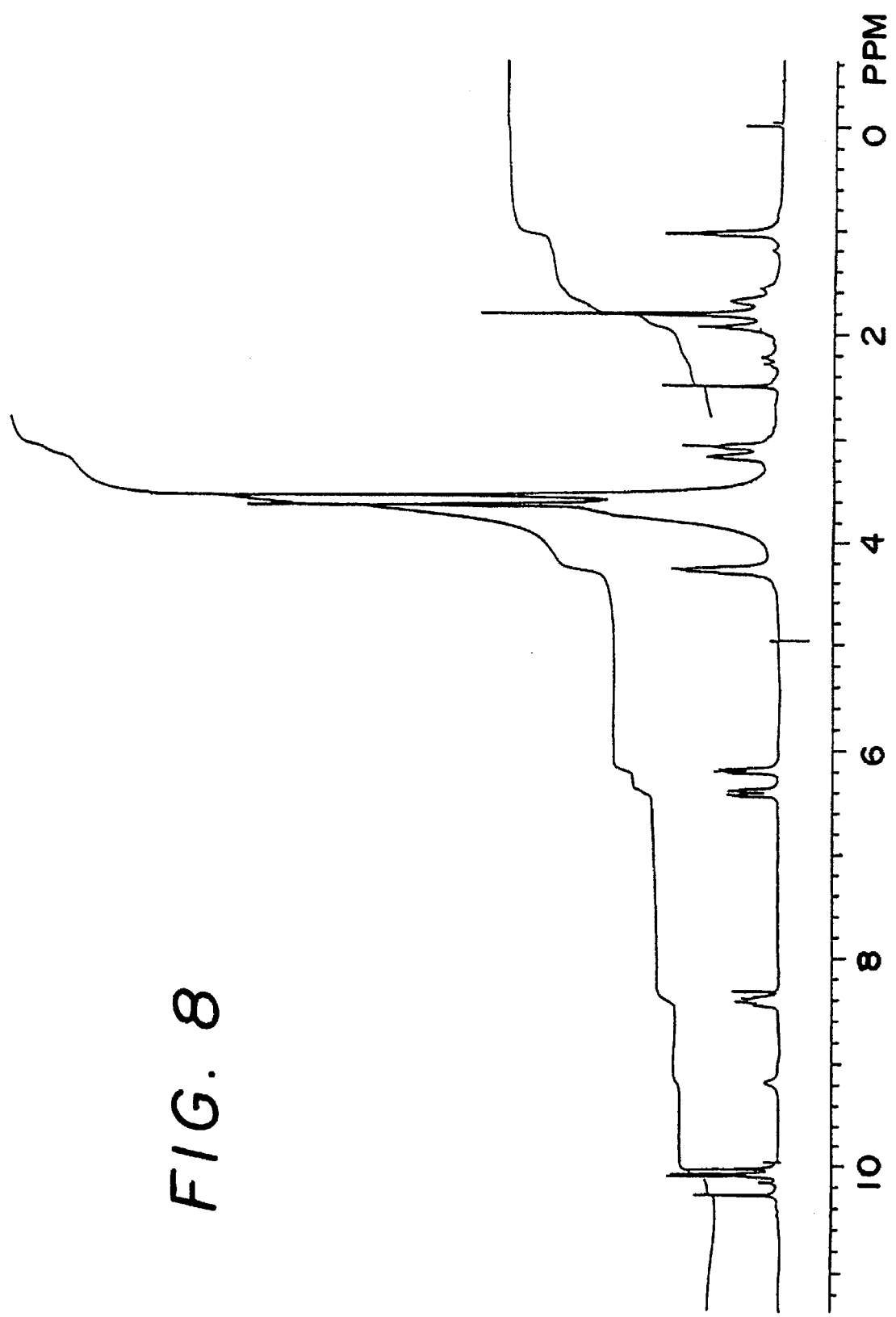
FIG. 8 illustrates a one-dimensional $^1$H-NMR of EDC-PP(A).
Figure 9:
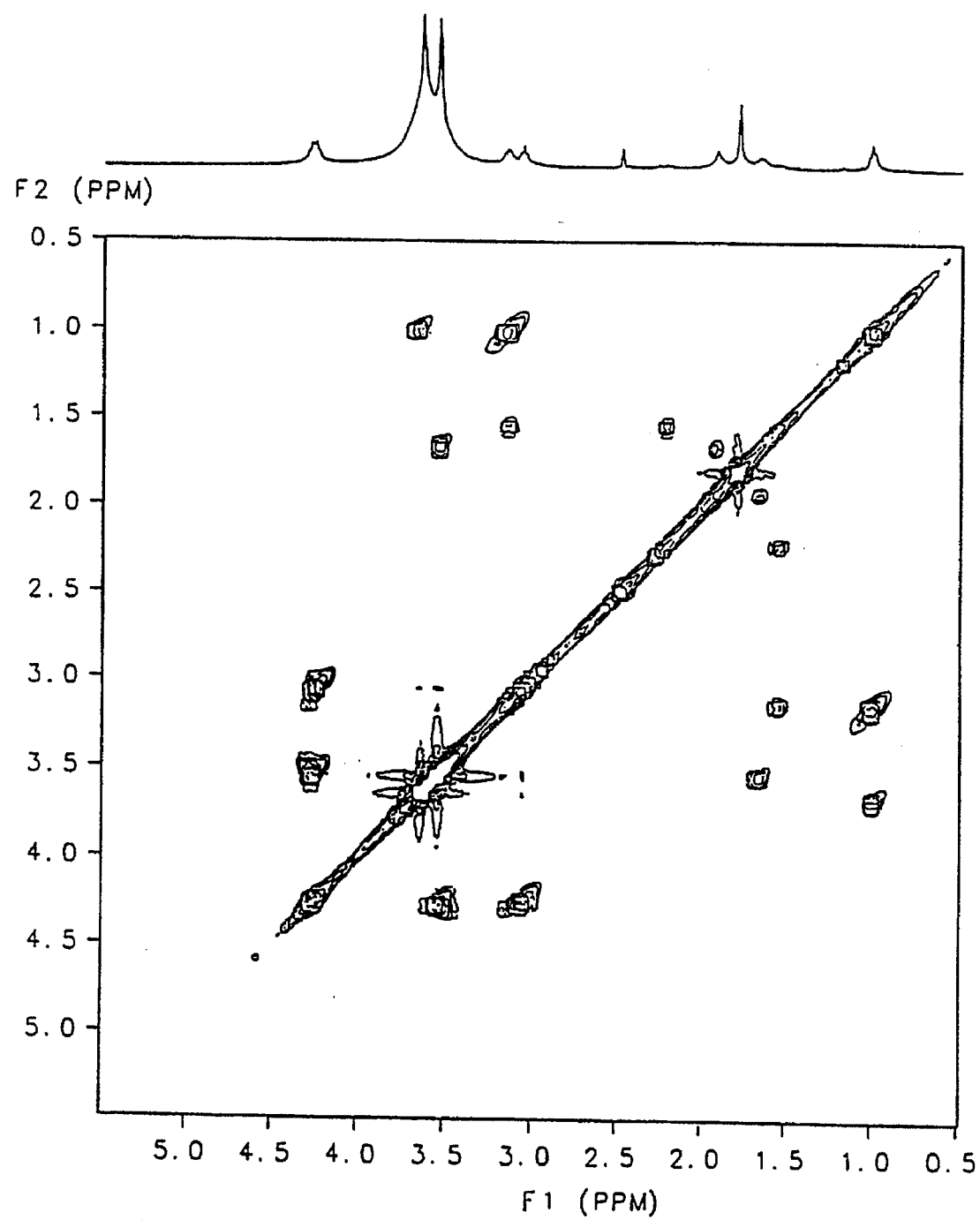
FIG. 9 illustrates a two-dimensional NMR (H-H COSY spectrum) of EDC-PP(A).
Figure 10:
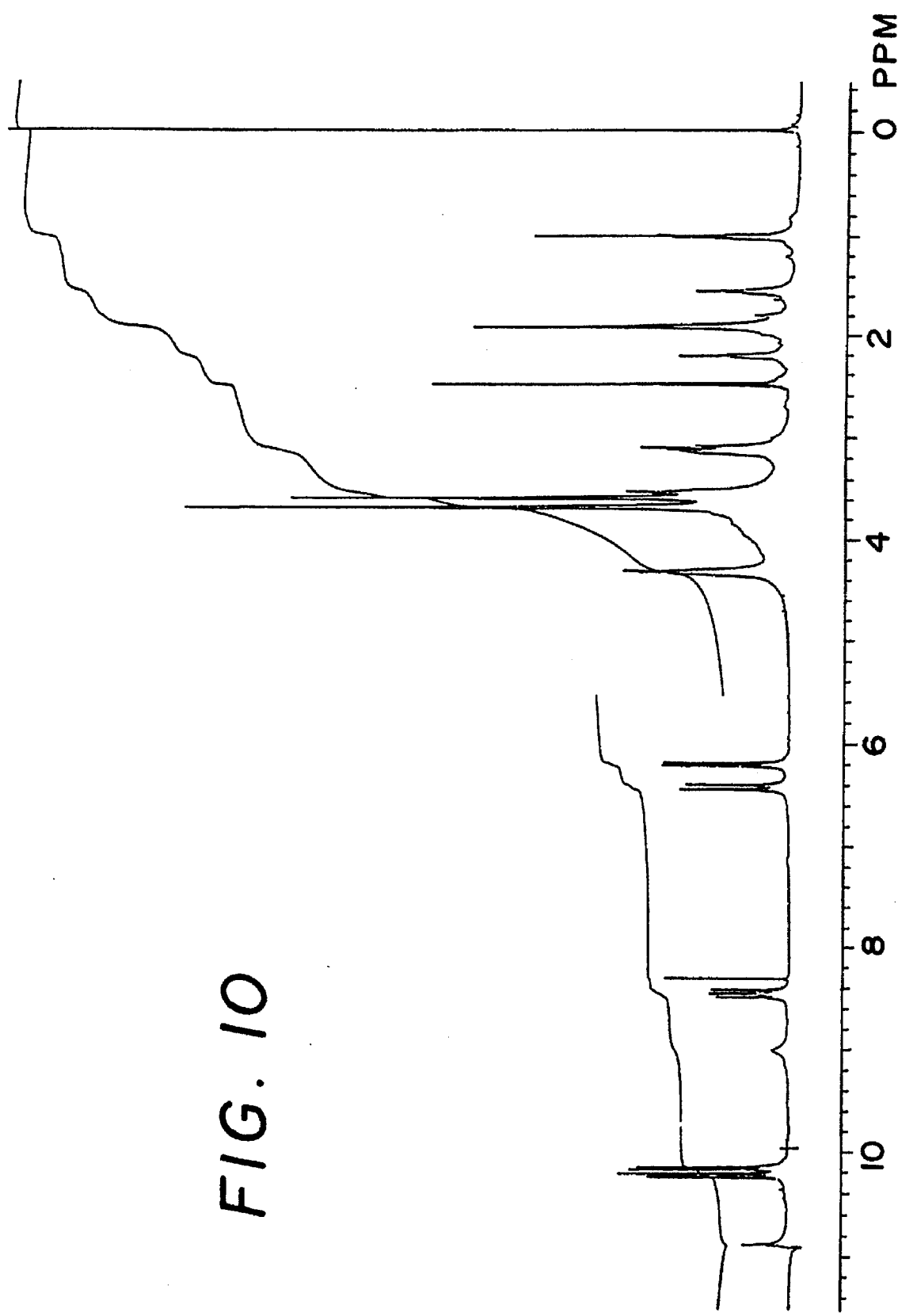
FIG. 10 illustrates a one-dimensional $^1$H-NMR of EDC-PP(B).
Figure 11:
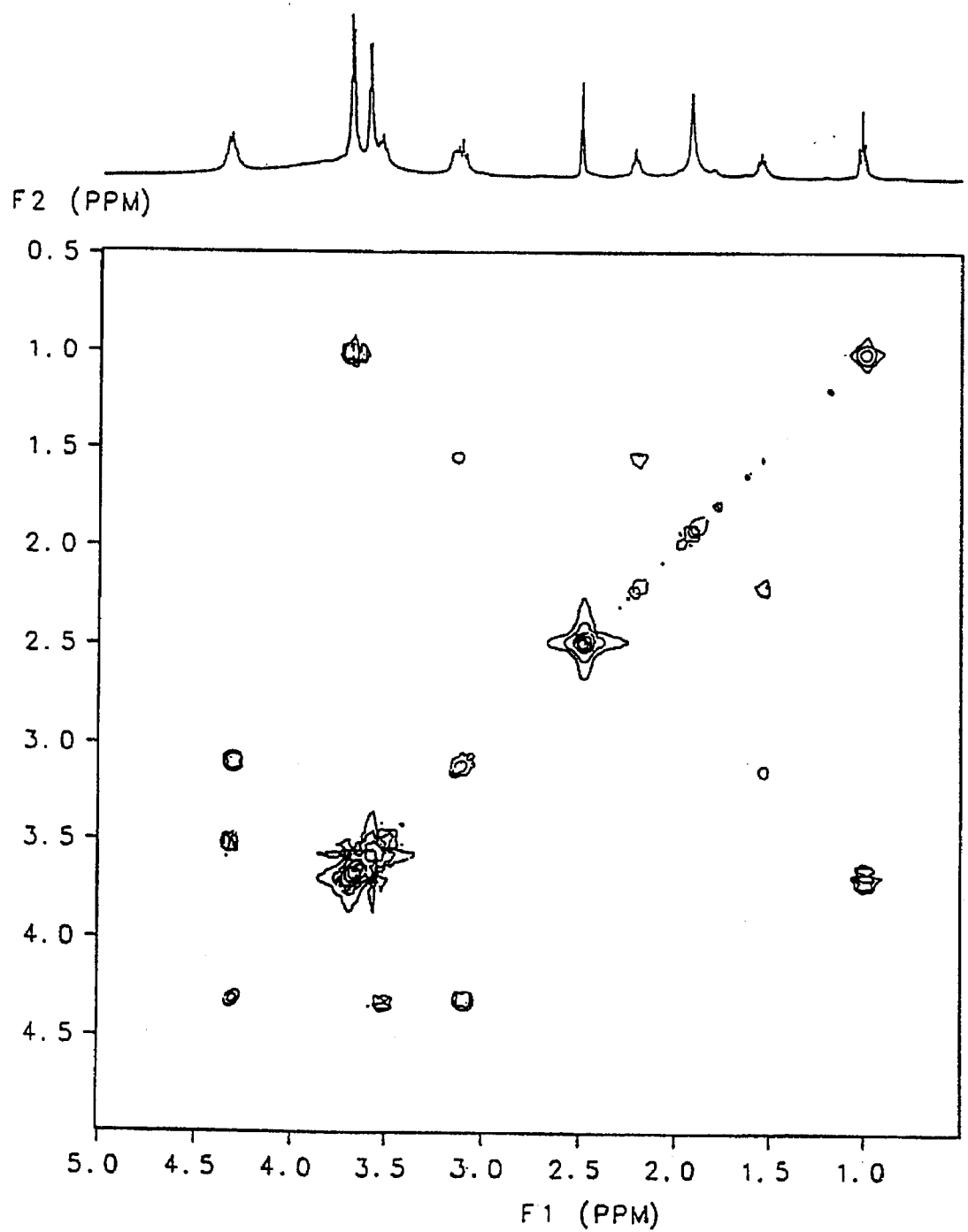
FIG. 11 illustrates a two-dimensional NMR (H-H COSY spectrum) of EDC-PP(B).

(2) Structure of 2EDC-Hemin:

$^1$H-NMR of 2EDC-Hemin was measured in the same manner as in Preparation Example 1. A one-dimensional spectrum of 2EDC-Hemin is illustrated in FIG. 6, and a COSY spectrum in FIG. 7. From the analysis of these spectra, the thus-obtained compound was found to have a structure that EDC was bonded by an amide linkage to the carboxyl groups of the carboxyethyl groups at both 13- and 17-positions of hemin. Incidentally, since EDC has two imide groups (—N=C—), there are 4 structural isomers in 2EDC-Hemin. The 2EDC-Hemin thus obtained is presumed to be a mixture of these compounds.

Preparation Example 3 (Synthesis of EDC-PP):
(1) Synthesis of EDC-PP:

After 900 mg of PP were dissolved in 100 ml of 0.1M $Na_2B_4O_7$ (pH 9.6) at room temperature, 1,850 mg of EDC in the form of powder were added thereto. The mixture was stirred for 30 minutes at room temperature as is, and then dialyzed to water through a dialysis membrane (molecular weight cut-off value: 12K–14K) produced by Spectrum Company for 2 days. The dialyzate was then lyophilized, thereby obtaining 970 mg of dry powder.

Subsequently, the dry powder was purified by means of CPC. Using a solvent system composed of chloroform:methanol:water=360:140:500, a sample was dissolved in 3 ml of a chloroform layer, a chloroform layer was used as a mobile phase to monitor the absorbance at 400 nm under conditions of a flow rate of 5 ml/min and the number of rotor revolutions of 600 rpm, and the eluate was fractionated into 10-ml portions. Fraction Nos. 5 to 45 in which absorption was observed were collected to concentrate them by a rotary evaporator.

Then, 100 g of silica gel were charged into a column of 25 mm in diameter and 600 mm in length, and a sample was added to the column. Fractions were collected in 500-ml portions. The compositions of eluents were as follows:

|   | Chloroform | Methanol | Acetic acid |
|---|---|---|---|
| 1 | 500 | 0 | 5 |
| 2 | 480 | 20 | 5 |
| 3 | 460 | 40 | 5 |
| 4 | 440 | 60 | 5 |
| 5 | 420 | 80 | 5 |
| 6 | 400 | 100 | 5 |
| 7 | 350 | 150 | 5 |
| 8 | 300 | 200 | 5 |

A fraction 6 (Fraction A) and a fraction 7 (Fraction B) obtained by thin layer chromatography were separately concentrated and lyophilized, thereby obtaining 260.1 mg of EDC-PP(A) from Fraction A and 125.4 mg of EDC-PP(B) from Fraction B.

(2) Structure of EDC-PP:

$^1$H-NMRs of EDC-PP(A) and EDC-PP(B) are shown in FIGS. 8, 9, 10 and 11. Incidentally, the measuring conditions for $^1$H-NMR are the same as those for EDC-Hemin except that $SnCl_2$ was not used.

Figure 12:
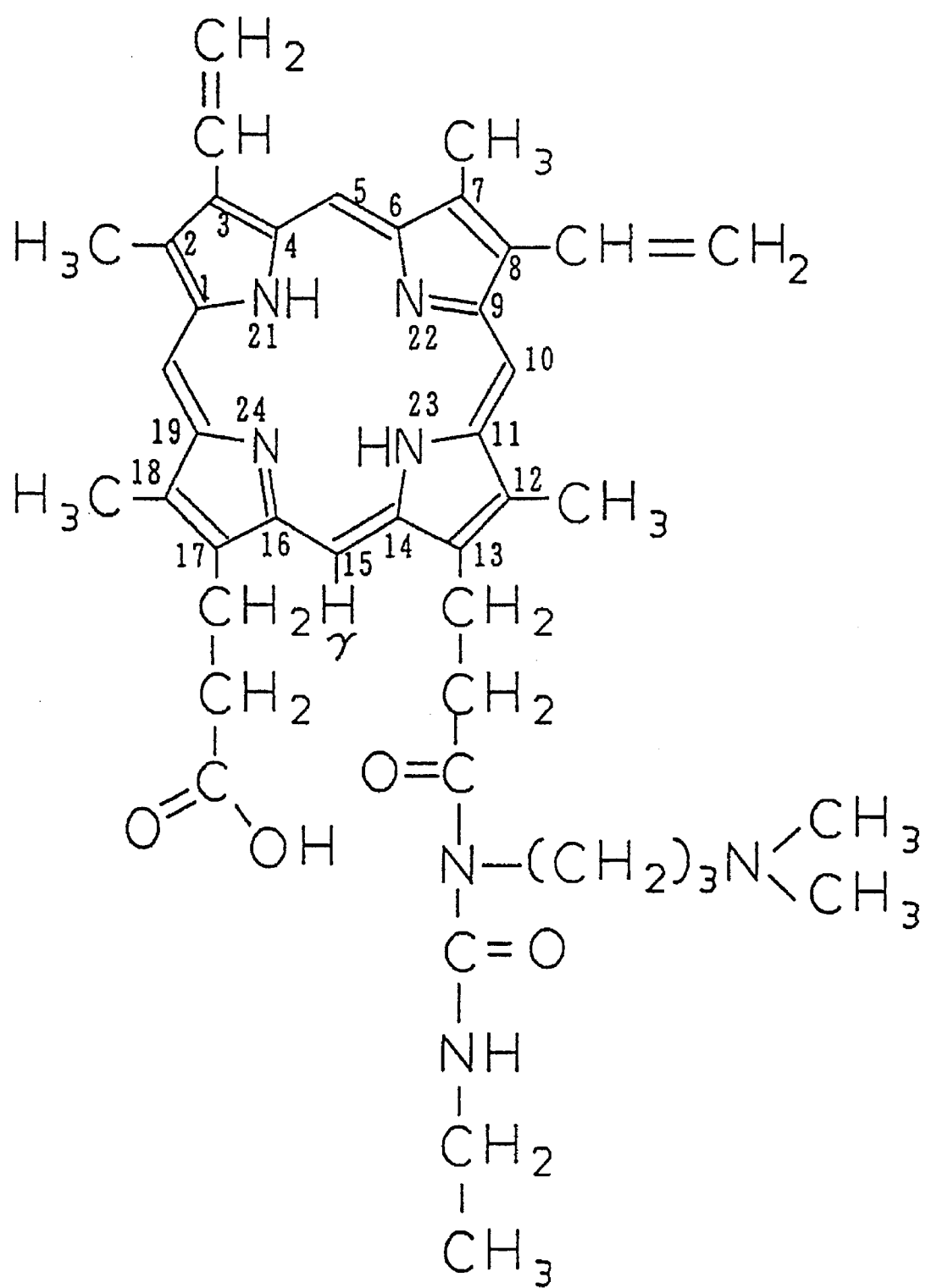
FIG. 12 illustrates a chemical structural formula of a main component (¾) of EDC-PP(A).
Figure 13:
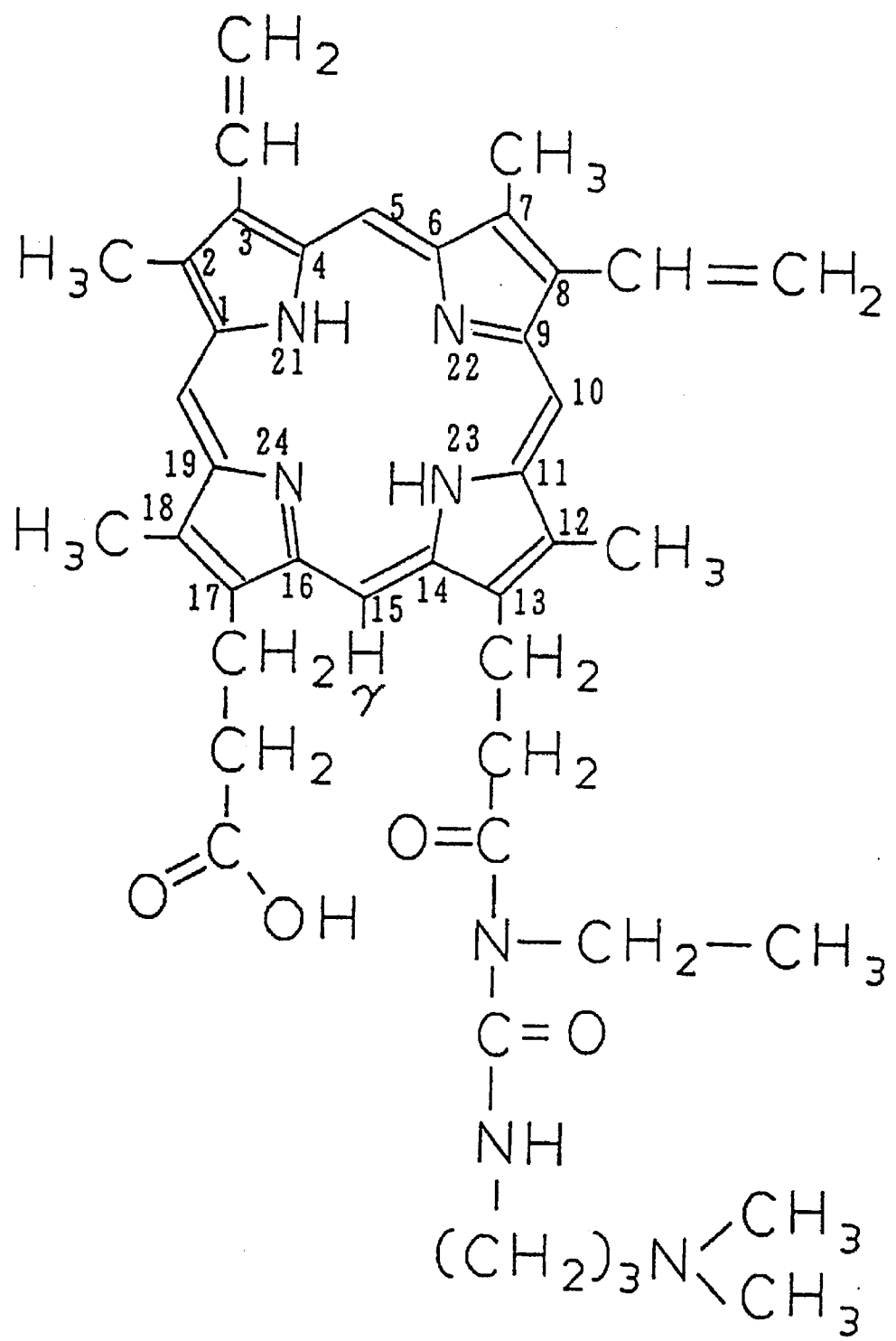
FIG. 13 illustrates a chemical structural formula of a ¼-component of EDC-PP(A), and EDC-PP(B).

(a) EDC-PP(A):

From an H-H COSY spectrum (two-dimensional), EDC-PP(A) is a compound in which the N-N'-dimethylaminopropylamino moiety (FIG. 12) or ethylamino moiety (FIG. 13) in EDC was bonded by an amide linkage to the carboxyl group of the carboxyethyl group on either 13-C or 17-C of hemin. The production ratio of the compound in FIG. 12 to the compound in FIG. 13 is about 3:1 from the integral ratio of the $^1$H-NMR.

(b) EDC-PP(B):

A structural analysis was conducted in the same manner as in EDC-PP(A). As a result, it was found that EDC-PP(B) has a structure illustrated in FIG. 13. However, the compound illustrated in FIG. 13 and belonging to EDC-PP(A) differs from EDC-PP(B) in Rf value on TLC, and these compounds are considered to be cis-trans isomers about the NH—CO linkage of EDC-urea.

Preparation Example 4 (Synthesis of EDC-Fe-MesoP):
(1) Synthesis of Fe-mesoporphyrin:

In 150 ml of acetic acid and 3 ml of pyridine, were dissolved 300 ml of mesoporphyrin (product of Porphyrin Products Company), to which 37.5 mg of $FeCl_3.6H_2O$ (product of Kanto Chemical Co., Inc.) dissolved in 4.5 ml of pyridine were slowly added dropwise. The mixture was stirred for 5 days at 90° C. by a magnetic stirrer. Thereafter, a reaction product was confirmed by TLC (thin layer chromatography), and poured into 750 ml of ethyl acetate. The precipitate was washed each twice with 10% hydrochloric acid, 25% saline and deionized water, and then concentrated by a rotary evaporator, thereby obtaining 188.9 mg of solid matter. Then, the solid matter was dissolved in 2 ml of chloroform to subject to chromatography on a silica gel column (40 g) of 20 mm in diameter and 300 mm in length. Elution was conducted with 500 ml of chloroform and then with an eluent having a composition of chloroform:methanol:acetic acid=90:10:1 to collect the eluate in 30-ml portions. Each fraction was spotted by TLC and developed with a solvent having a composition of chloroform:methanol:acetic acid=90:10:1. Fractions containing the intended product were concentrated by a rotary evaporator to obtain 101 mg of Fe-mesoporphyrin.

(2) Synthesis of EDC-Fe-MesoP:

In 12 ml of 0.1M $Na_2B_4O_7$ (pH 9.6), were dissolved 80 mg of Fe-mesoporphyrin and 200 mg of EDC (product of Dojindo Laboratories). The resultant solution was stirred overnight at room temperature by means of a magnetic stirrer. The reaction mixture was dialyzed to deionized water through a dialysis membrane (molecular weight cut-off: 3,500) produced by Spectrum Company for 2 days. The dialyzate was then lyophilized, thereby obtaining 93.1 mg of dry powder.

The dry powder in an amount of 93.1 mg was dissolved in a solvent for development and subjected to chromatography on a silica gel column (18 g) of 20 mm in diameter and 600 mm in length. As the development solvent, that having a composition of chloroform:methanol:acetic acid=90:10:1. The eluate was fractionated and collected in 80-ml portions, and Fractions 9 to 15 were concentrated by a rotary evaporator and dialyzed. The dialyzate was then lyophilized to obtain 4.8 mg of EDC-Fe-MesoP.

Figure 14:
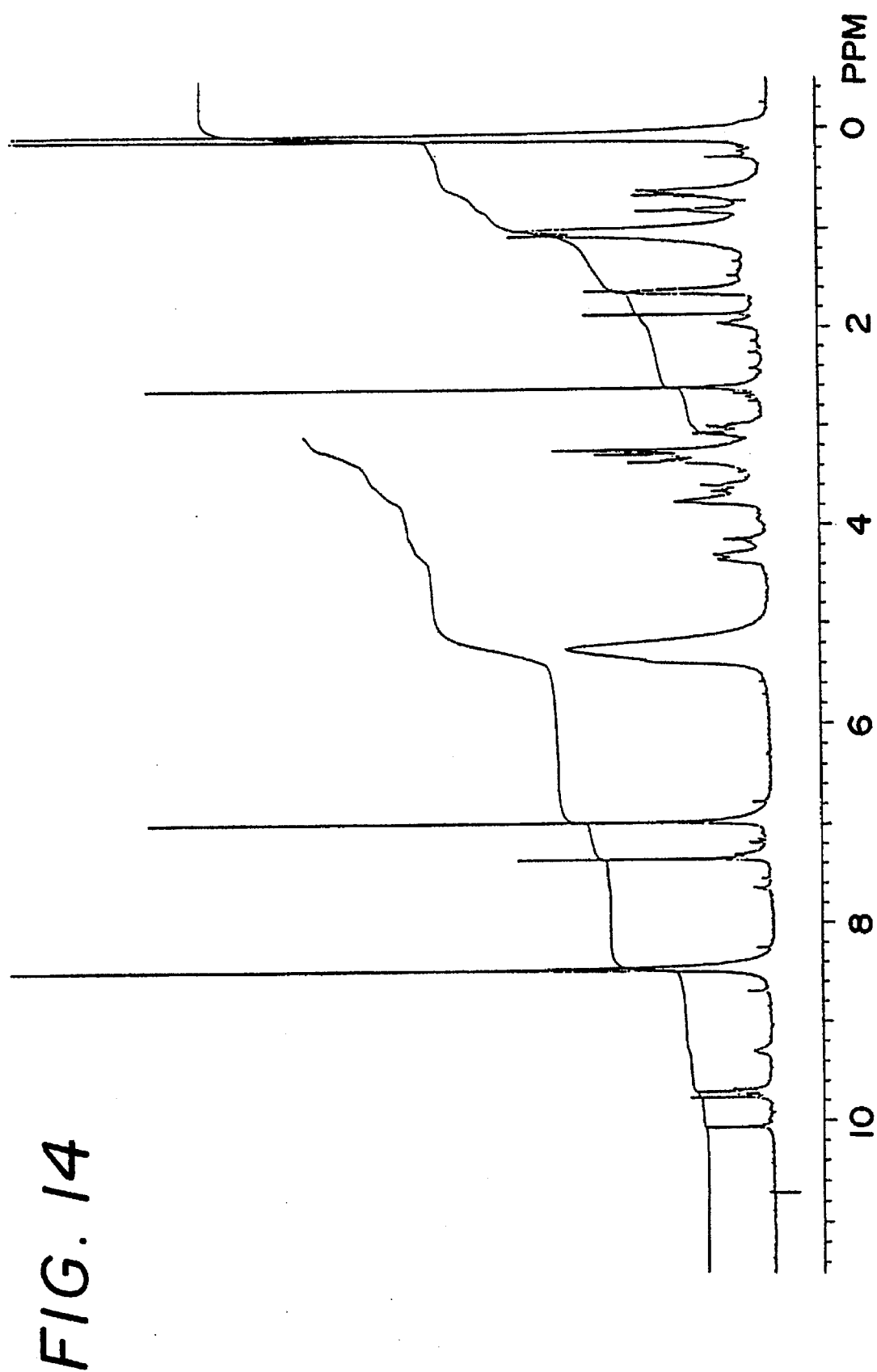
FIG. 14 illustrates a one-dimensional $^1$H-NMR of EDC-Fe-MesoP.
Figure 15:
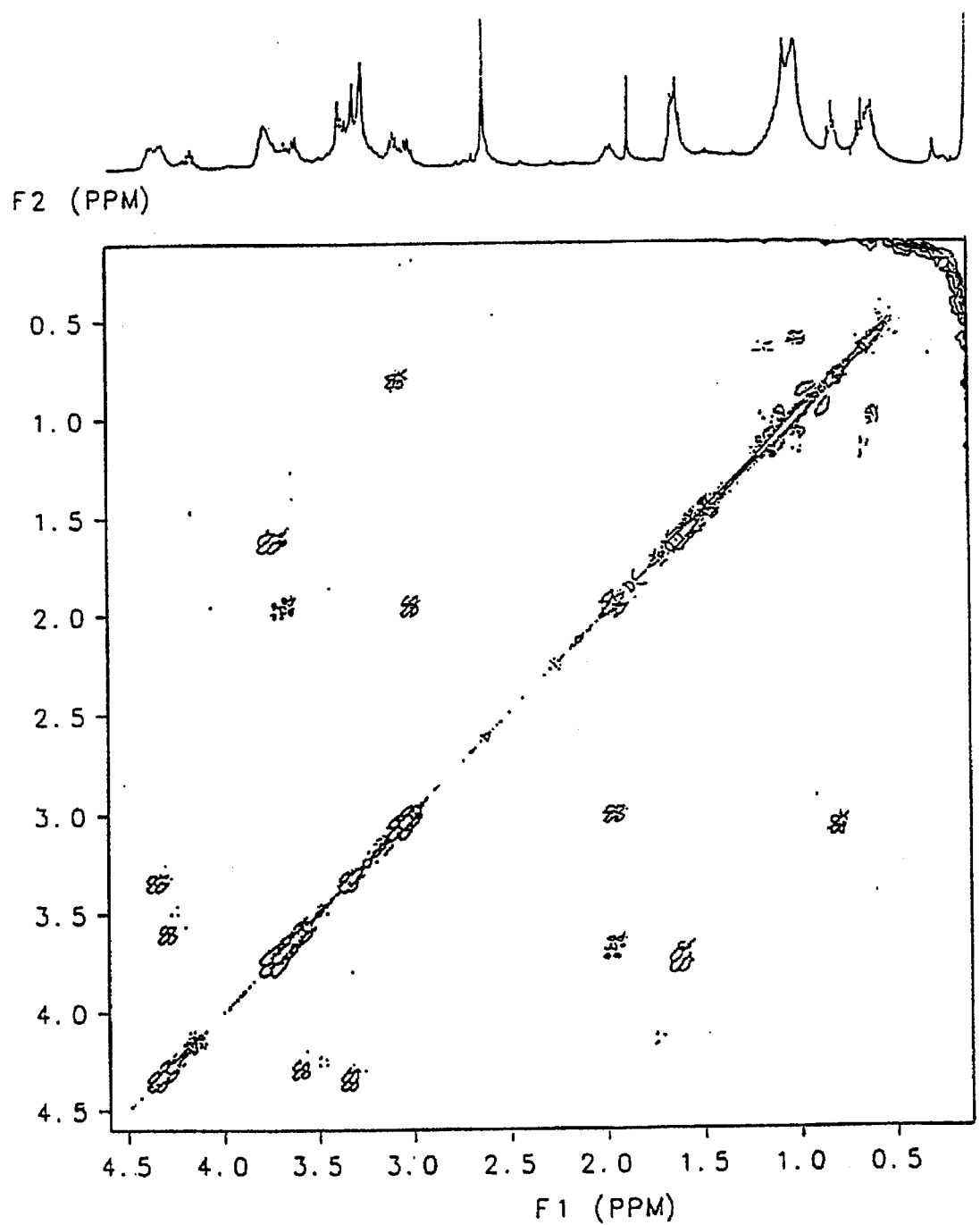
FIG. 15 illustrates a two-dimensional NMR (H-H COSY spectrum) of EDC-Fe-MesoP.

(3) Structure of EDC-Fe-MesoP:

$^1$H-NMR of EDC-Fe-MesoP was measured in the same manner as in Preparation Example 1. A one-dimensional spectrum of 2EDC-Hemin is illustrated in FIG. 14, and a COSY spectrum in FIG. 15. From the analysis of these spectra, the thus-obtained compound was found to be a mixture of compounds in which the dimethylaminopropylamino moiety in EDC was bonded by an amide linkage to the carboxyl group on either C-13 or C-17 of Fe-MesoP.

Preparation Example 5 (Synthesis of CDC-Hemin):

(1) Synthesis of CDC-Hemin:

In 100 ml of 0.1M $Na_2B_4O_7$ (pH 9.6), were dissolved 1 g of hemin (product of Tokyo Kasei Kogyo Co., Ltd.) and 1.5 g of CDC (product of Kanto Chemical Co., Inc.). The resultant solution was stirred for 30 minutes at room temperature by means of a magnetic stirrer. After the reaction mixture was dialyzed to deionized water through a dialysis membrane (molecular weight cut-off: 12K–14K) produced by Spectrum Company for 2 days, the dialyzate was lyophilized, thereby obtaining 2.82 g of dry powder.

The dry powder in an amount of 770 mg was dissolved in a solvent composed of chloroform:methanol:acetic acid= 96:4:1 and subjected to chromatography on a silica gel column (100 g) of 25 mm in diameter and 600 mm in length. As solvents, those having a composition of chloroform: methanol:acetic acid=96:4:1 to 68:32:1. The eluate was collected in 200-ml portions, and Fractions 6 to 8 and Fractions 12 to 13 were concentrated as Fraction A and Fraction B, respectively, by a rotary evaporator and dialyzed. The dialyzates were then lyophilized to obtain 55.2 mg of CDC-Hemin(A) and 4.1 mg of CDC-Hemin(B).

(2) Structure of CDC-Hemin:

$^1$H-NMRs of CDC-Hemin(A) and CDC-Hemin(B) were measured in the same manner as in Preparation Example 1.

Figure 16:
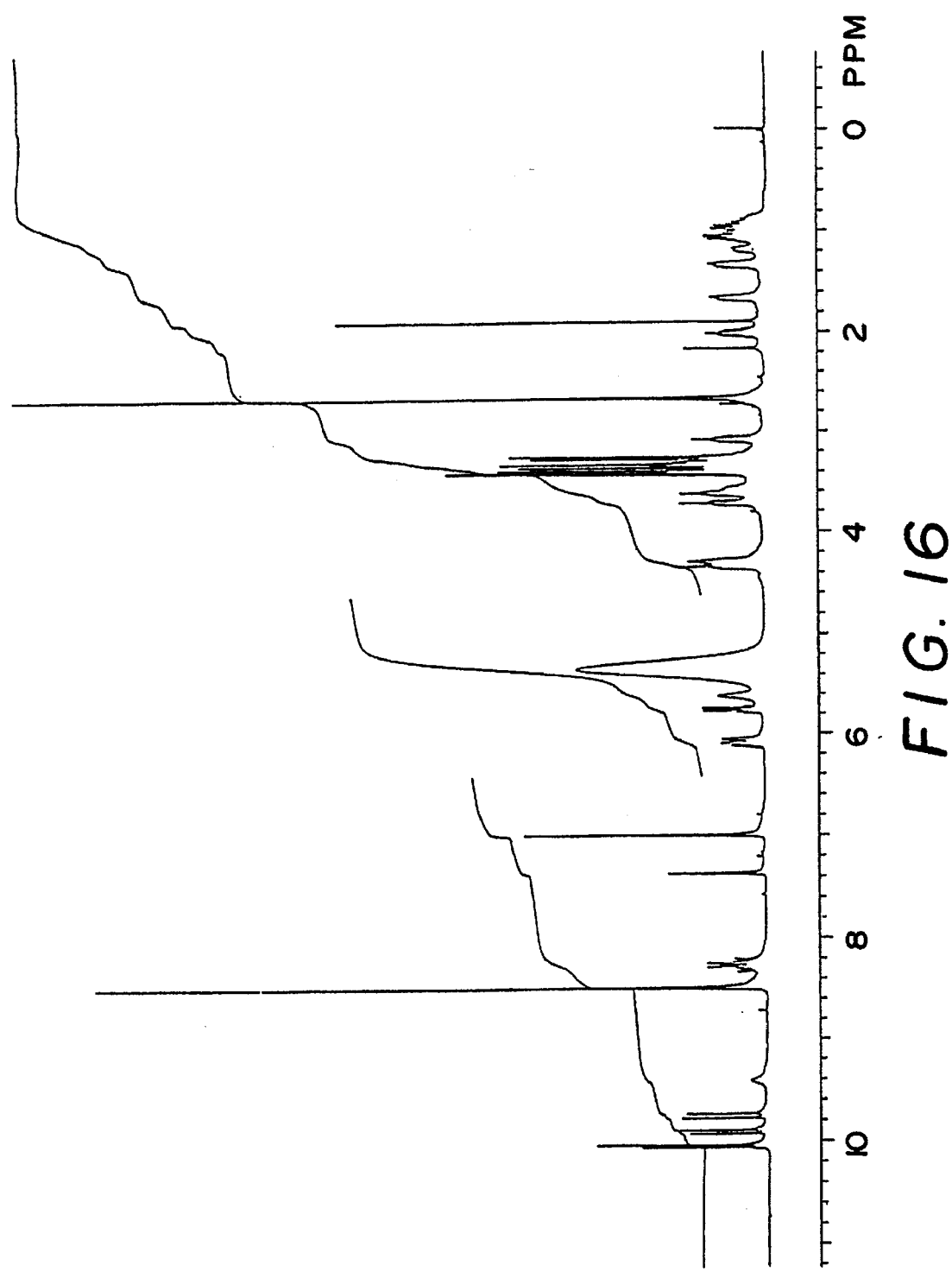
FIG. 16 illustrates a one-dimensional $^1$H-NMR of CDC-Hemin(A).
Figure 17:
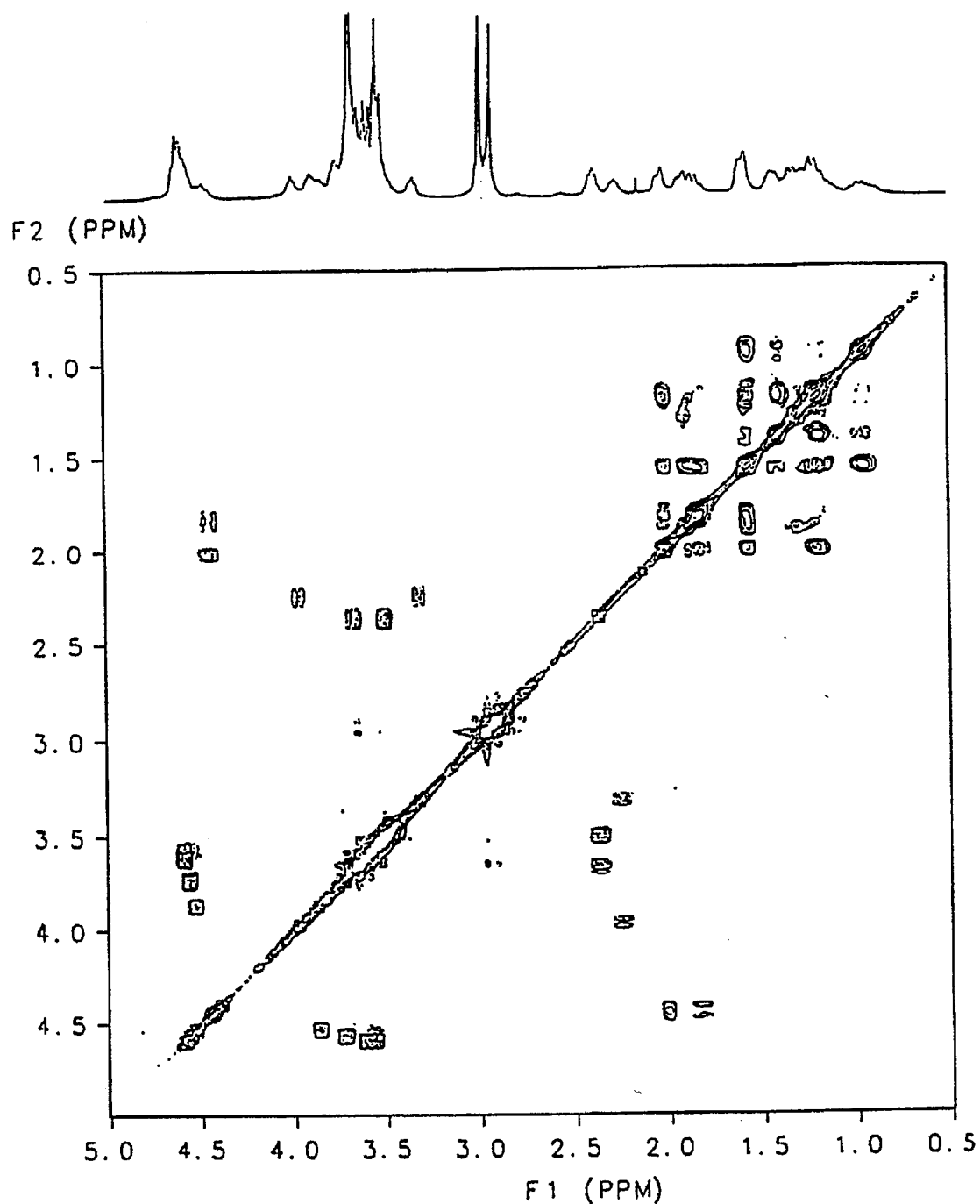
FIG. 17 illustrates a two-dimensional NMR (H-H COSY spectrum) of CDC-Hemin(A).

(a) CDC-Hemin(A):

A one-dimensional spectrum of CDC-Hemin(A) is illustrated in FIG. 16, and a COSY spectrum in FIG. 17. From the analysis of these spectra, the thus-obtained compound was found to be a mixture of compounds in which the N,N-dimethylaminopropylamino moiety in CDC was bonded by an amide linkage to the carboxyl group on either C-13 or C-17 of Hemin.

Figure 18:
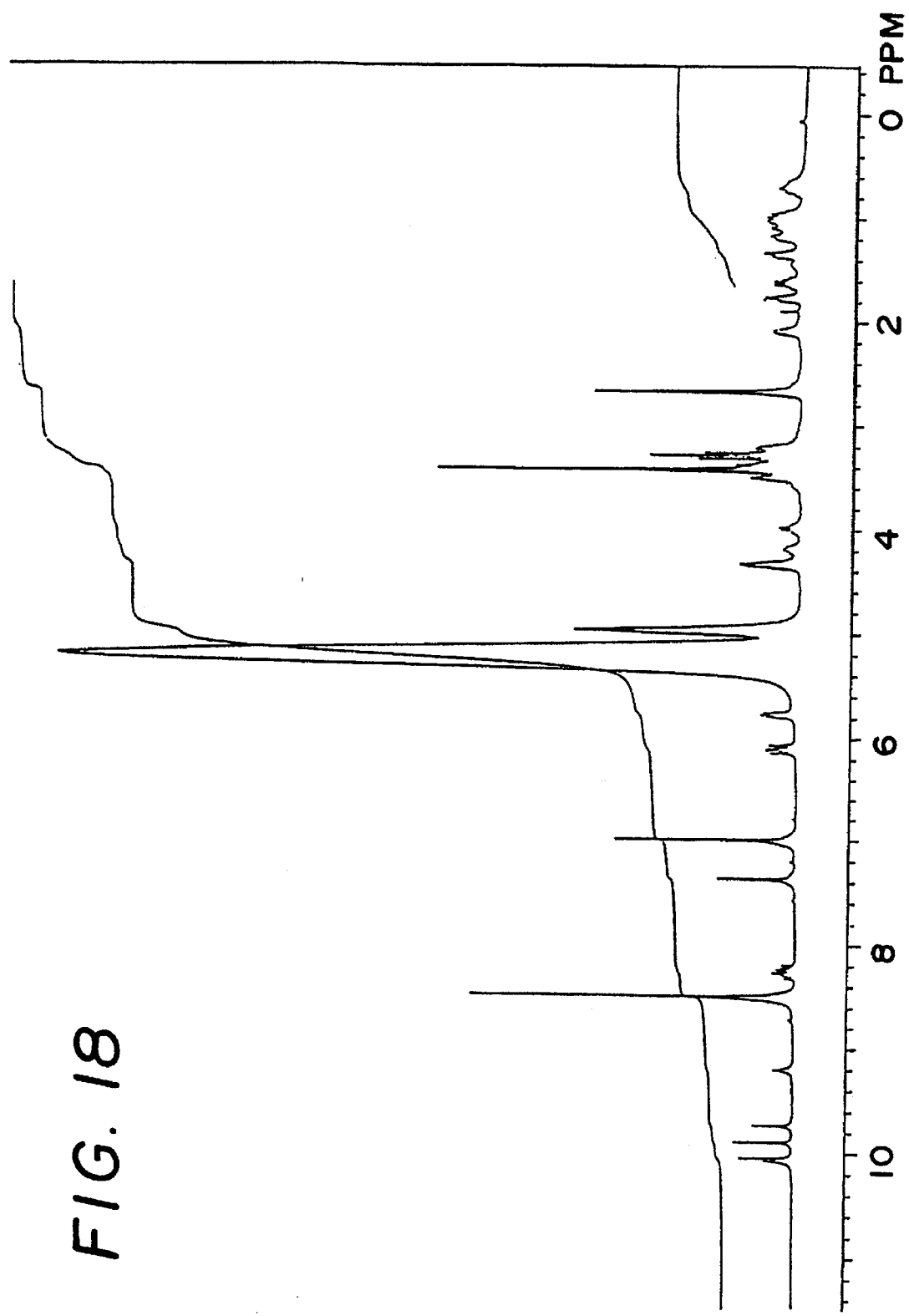
FIG. 18 illustrates a one-dimensional 1H-NMR of CDC-Hemin(B).
Figure 19:
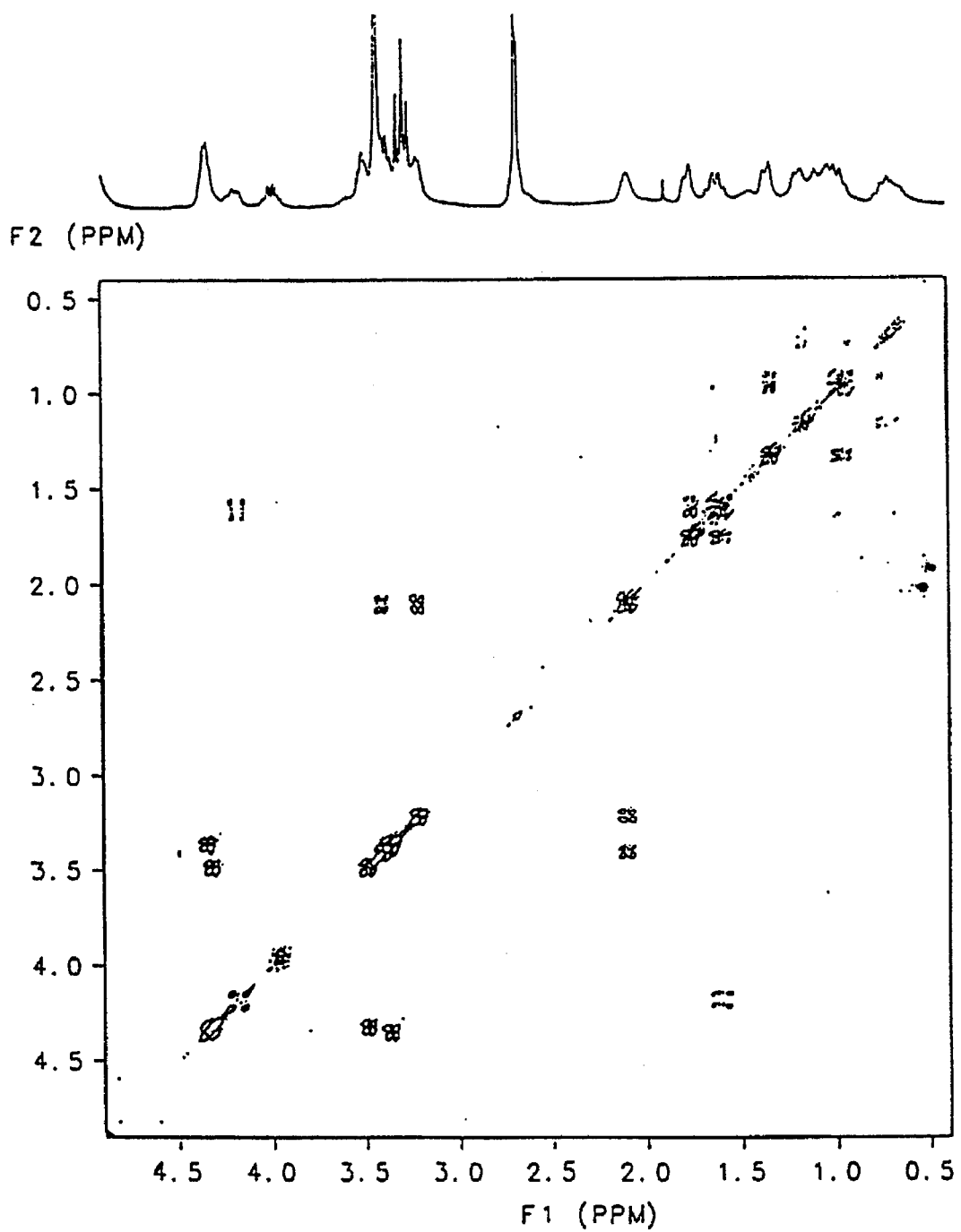
FIG. 19 illustrates a two-dimensional NMR (H-H COSY spectrum) of CDC-Hemin(B).

(b) CDC-Hemin(B):

A one-dimensional spectrum of CDC-Hemin(B) is illustrated in FIG. 18, and a COSY spectrum in FIG. 19. From the analysis of these spectra, the thus-obtained compound was found to be a mixture of compounds in which the cyclohexylamino moiety in CDC was bonded by an amide linkage to the carboxyl group on either C-13 or C-17 of Hemin.

Preparation Example 6 (Synthesis of IDC-Hemin):

(1) Synthesis of IDC-Hemin:

In 100 ml of N,N,-dimethylformamide, were dissolved 1 g of hemin (product of Tokyo Kasei Kogyo Co., Ltd.), 1.4 g of IDC (product of Kanto Chemical Co., inc.) and 210 μl of 3-dimethylamino-1-propanol (product of Tokyo Kasei Kogyo Co., Ltd.). The resultant solution was stirred for 6 days at room temperature by means of a magnetic stirrer. After the reaction mixture was dialyzed to deionized water through a dialysis membrane (molecular weight cut-off: 12K–14K) produced by Spectrum Company for 2 days, the dialyzate was lyophilized, thereby obtaining 970 mg of dry powder.

The dry powder in an amount of 970 mg was dissolved in a solvent composed of chloroform:methanol:acetic acid= 95:5:1 and subjected to chromatography on a silica gel column (100 g) of 25 mm in diameter and 600 mm in length. As solvents, those having a composition of chloroform: methanol:acetic acid=95:5:1 to 50:50:1. The eluate was collected in 100-ml portions, and Fractions 35 to 42 were concentrated by a rotary evaporator and dialyzed under the same conditions as described above. The dialyzate was then lyophilized to obtain 30.1 mg of IDC-Hemin.

Figure 20:
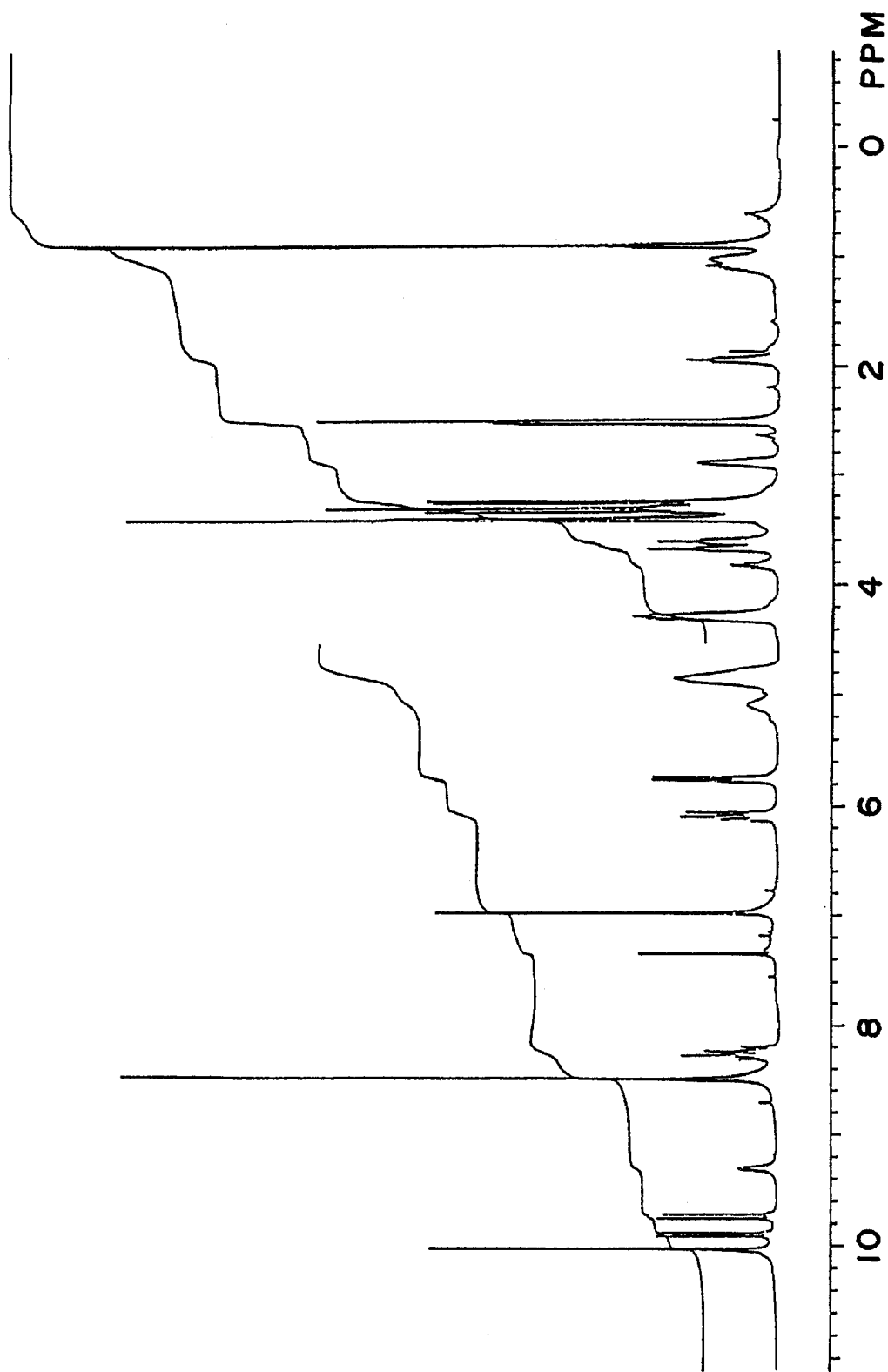
FIG. 20 illustrates a one-dimensional $^1$H-NMR of IDC-Hemin.
Figure 21:
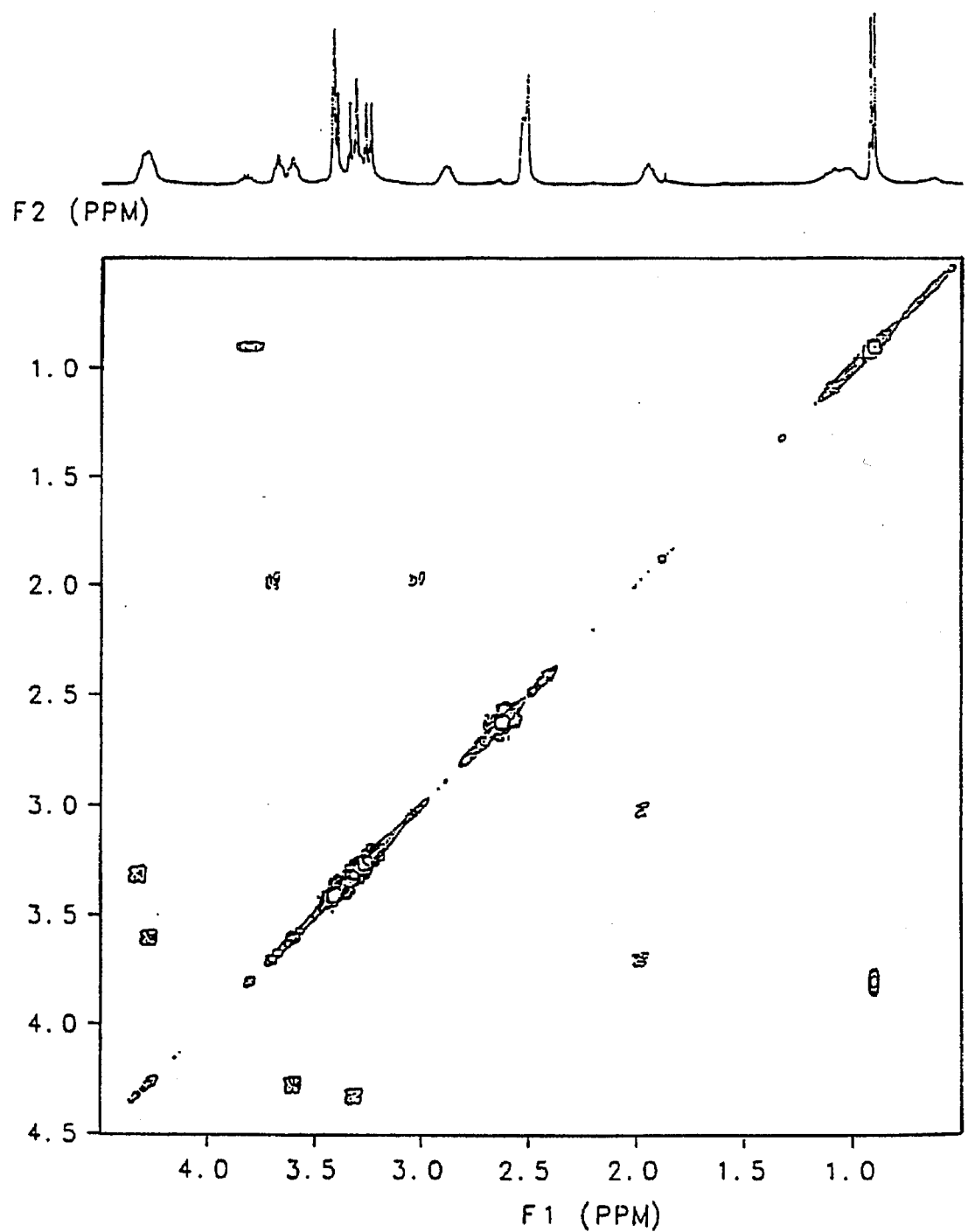
FIG. 21 illustrates a two-dimensional NMR (H-H COSY spectrum) of IDC-Hemin.

(2) Structure of IDC-Hemin:

$^1$H-NMR of IDC-Hemin was measured in the same manner as in Preparation Example 1. A one-dimensional spectrum of IDC-Hemin is illustrated in FIG. 20, and a COSY spectrum in FIG. 21. From the analysis of these spectra, the thus-obtained compound was found to be a mixture of compounds in which the dimethylaminopropylamino moiety in IDC was bonded by an amide linkage to the carboxyl group on either C-13 or C-17 of Hemin.

Preparation Example 7 (Synthesis of DMEA-Hemin):

(1) Synthesis of DMEA-Hemin:

In 100 ml of DMF, were dissolved 1 g of hemin (product of Tokyo Kasei Kogyo Co., Ltd.), 196 μl of N,N-dimethylethylenediamine (product of Tokyo Kasei Kogyo Co., Ltd.) and 1 g of EDC (product of Dojindo Laboratories). The resultant solution was stirred for 90 minutes at room temperature by means of a magnetic stirrer. The reaction mixture was dialyzed to deionized water through a dialysis membrane (molecular weight cut-off: 12K–14K) produced by Spectrum Company for 2 days, thereby obtaining 800 mg of dry powder.

The dry powder in an amount of 800 mg was dissolved in a solvent composed of chloroform:methanol:acetic acid= 96:4:1 and subjected to chromatography on a silica gel column (100 g) of 25 mm in diameter and 600 mm in length. As solvents, those having a composition of chloroform: methanol:acetic acid=96:4:1 to 50:50:1. The eluate was collected in 100-ml portions, and Fractions 24 to 32 were concentrated by a rotary evaporator and dialyzed under the same conditions as described above. The dialyzate was then lyophilized to obtain 237.8 mg of DMEA-Hemin.

Figure 22:
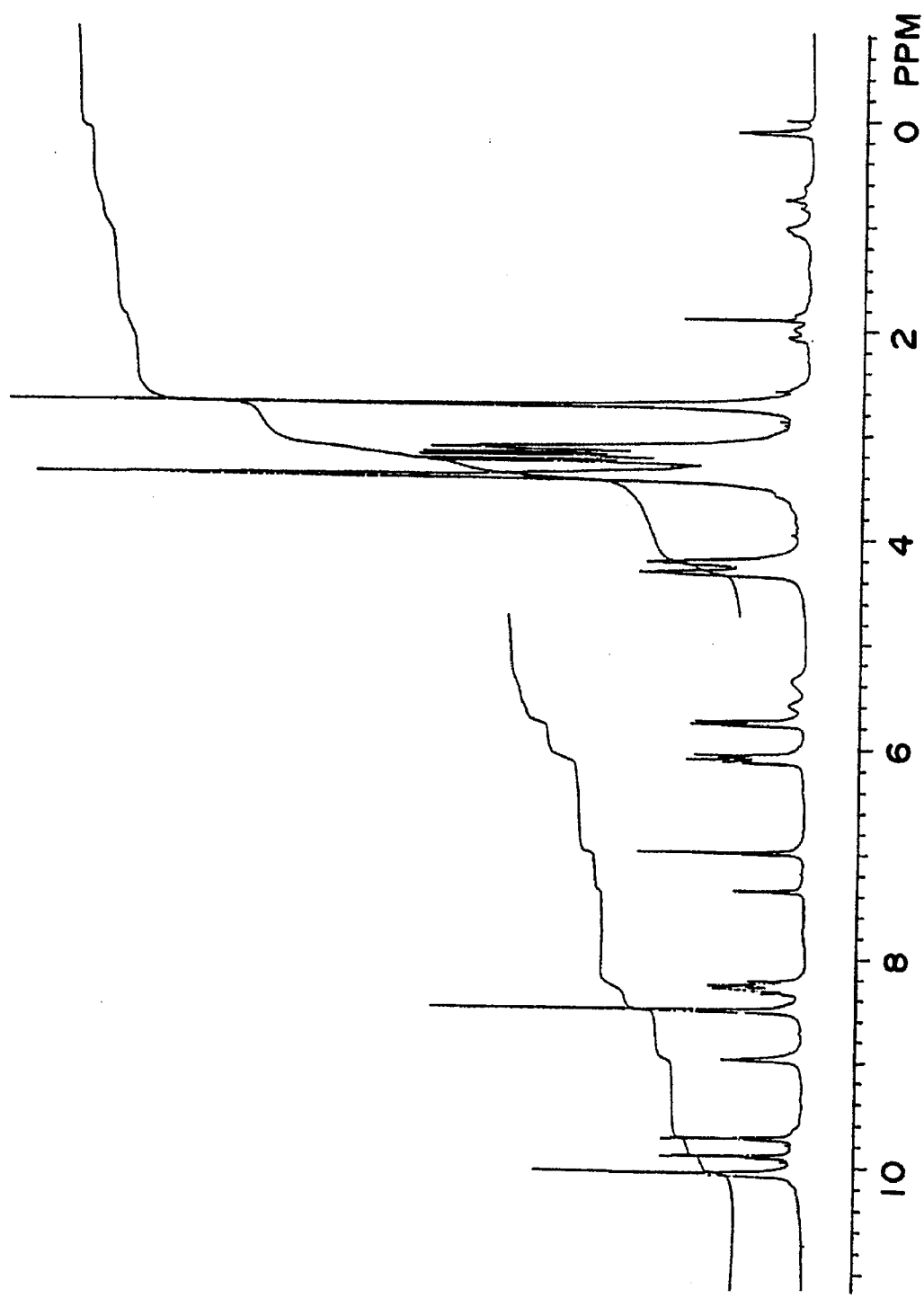
FIG. 22 illustrates a one-dimensional $^1$H-NMR of DMEA-Hemin.
Figure 23:
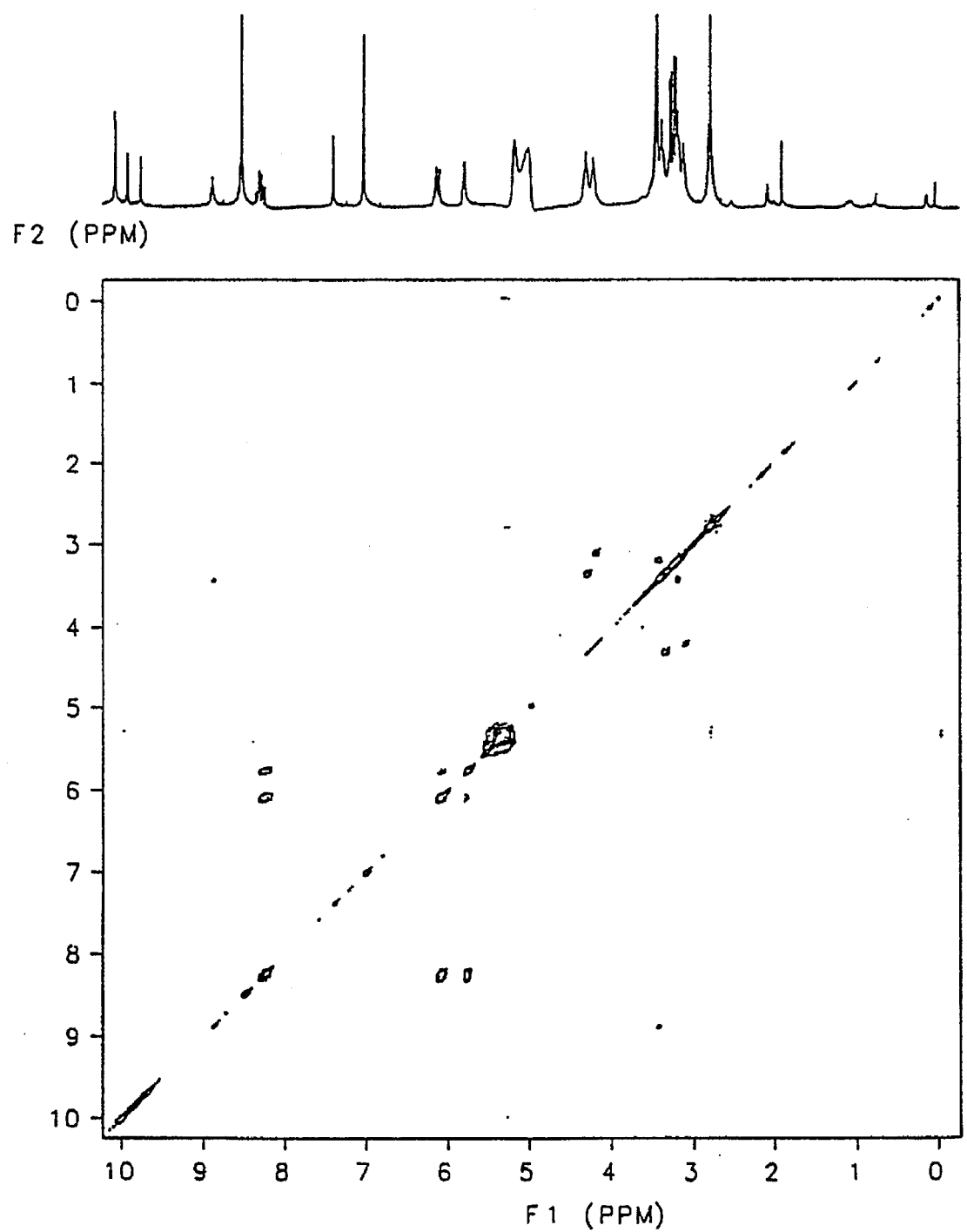
FIG. 23 illustrates a two-dimensional NMR (H-H COSY spectrum) of DMEA-Hemin.

(2) Structure of DMEA-Hemin:

$^1$H-NMR of DMEA-Hemin was measured in the same manner as in Preparation Example 1. A one-dimensional spectrum of DMEA-Hemin is illustrated in FIG. 22, and a COSY spectrum in FIG. 23. From the analysis of these spectra, the thus-obtained compound was found to be a mixture of compounds in which N,N-dimethylethylenediamine was bonded by an amide linkage to the carboxyl group on either C-13 or C-17 of Hemin.

Preparation Example 8 (Synthesis of PEG-Hemin):

(1) Synthesis of PEG-Hemin:

In 100 ml of DMF, were dissolved 1 g of hemin (product of Tokyo Kasei Kogyo Co., Ltd.), 9.2 g of polyethylene glycol methyl ether (MW 5,000, product of Aldrich) and 500 mg of EDC (product of Dojindo Laboratories). The resultant solution was stirred for 3 days at room temperature by means of a magnetic stirrer. The reaction mixture was dialyzed to deionized water through a dialysis membrane (molecular weight cut-off: 12K–14K) produced by Spectrum Company for 2 days, thereby obtaining 9.32 g of dry powder.

Two grams of the dry powder were subjected to chromatography on a silica gel column (100 g) of 25 mm in diameter and 600 mm in length. As solvents, those having a composition of chloroform:methanol:acetic acid=16:4:1 to 50:50:1. The eluate was collected in 200-ml portions, and Fractions 6 to 8 were concentrated by a rotary evaporator and dialyzed under the same conditions as described above. The dialyzate was then lyophilized to obtain 46.4 mg of PEG-Hemin.

Figure 24:
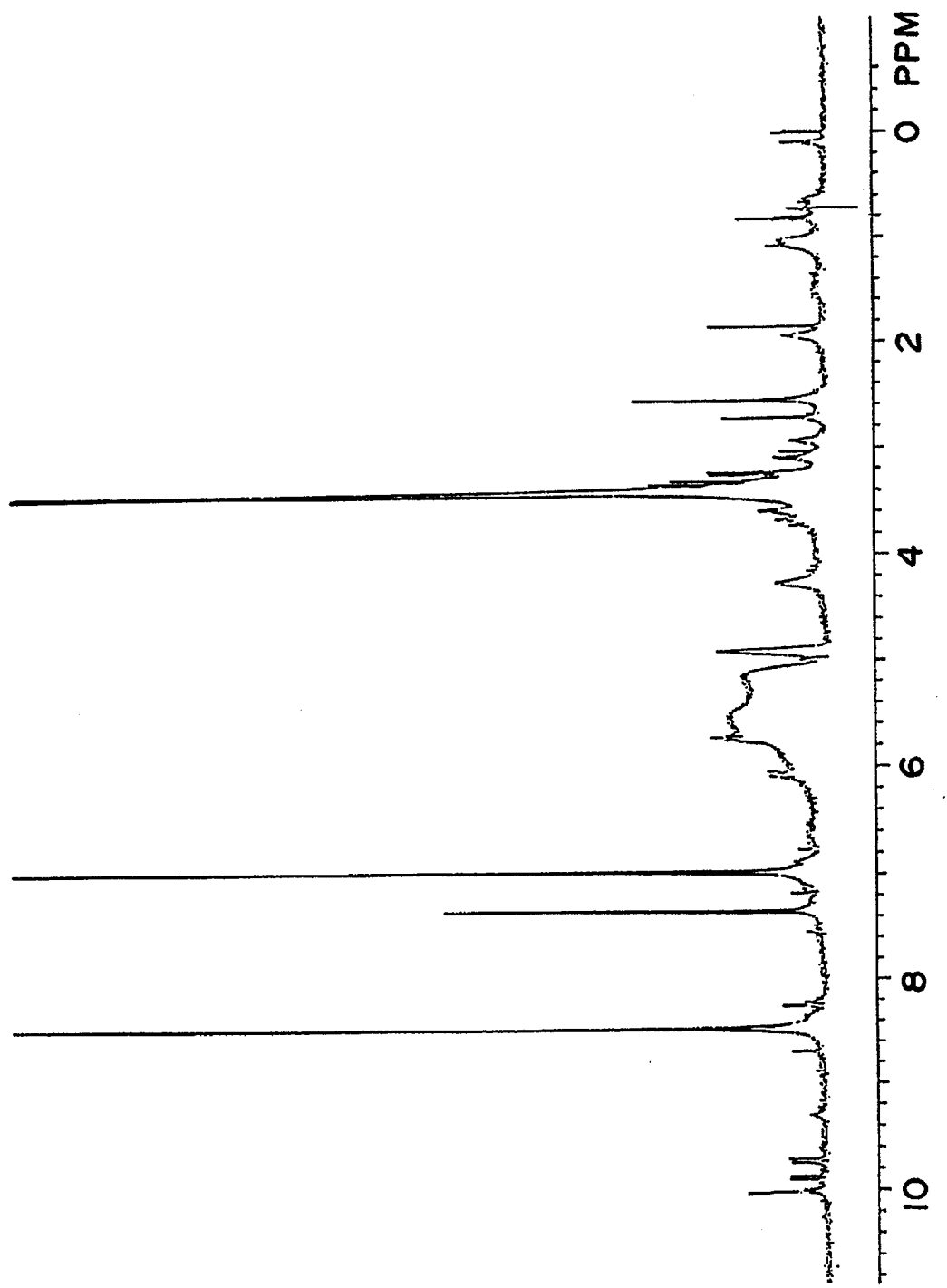
FIG. 24 illustrates a one-dimensional $^1$H-NMR of PEG-Hemin.
Figure 25:
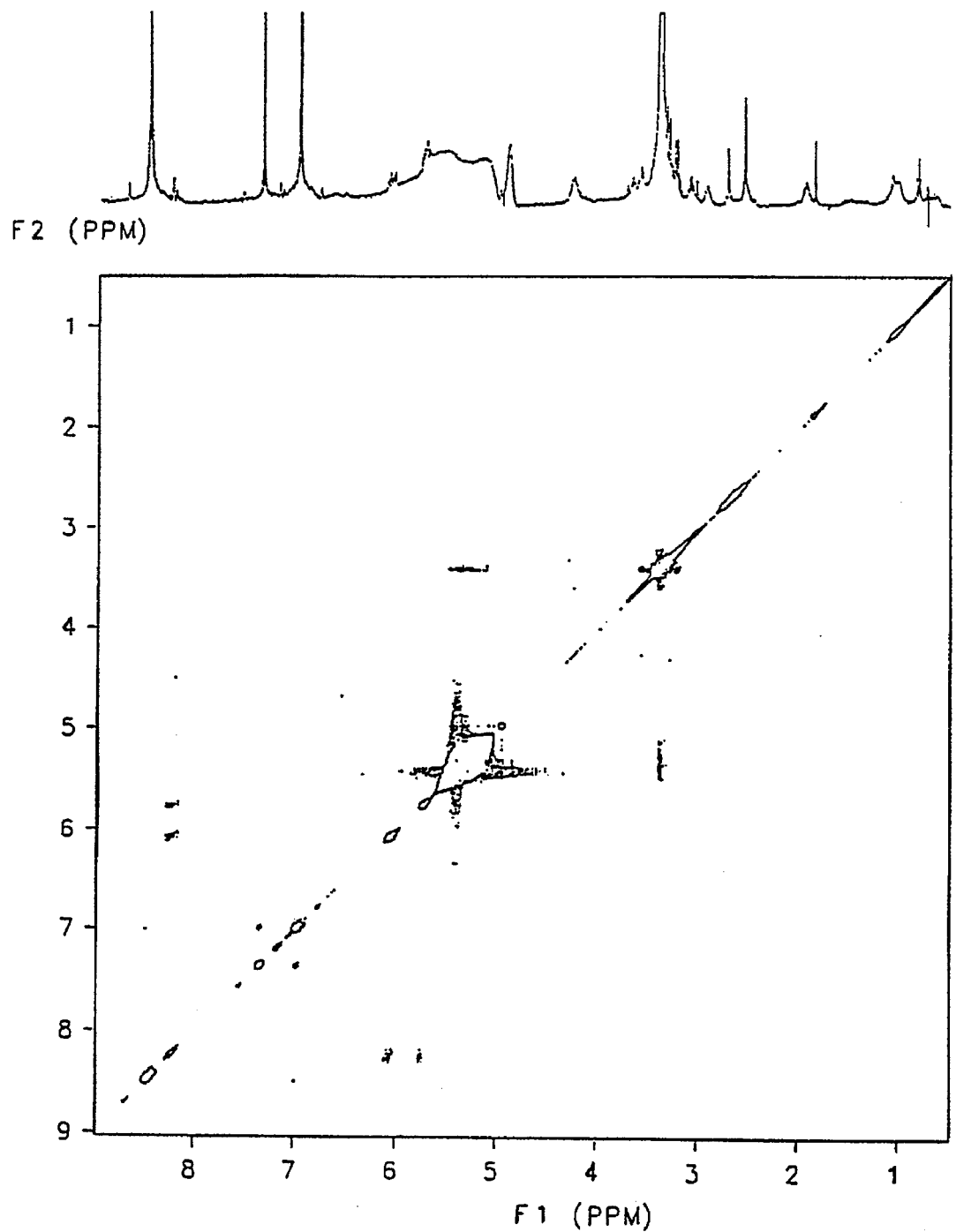
FIG. 25 illustrates a two-dimensional NMR (H-H COSY spectrum) of PEG-Hemin.

(2) Structure of PEG-Hemin:

$^1$H-NMR of PEG-Hemin was measured in the same manner as in Preparation Example 1. A one-dimensional spectrum of PEG-Hemin is illustrated in FIG. 24, and a COSY spectrum in FIG. 25. From the analysis of these spectra, the thus-obtained compound was found to be a mixture of compounds in which polyethylene glycol methyl ether was bonded by an ester linkage to the carboxyl group on either C-13 or C-17 of Hemin.

Preparation Example 9 (Synthesis of CDC-copper chlorophyllin(B)):

In 100 ml of 0.1M $N_2B_4O_7$ (pH 9.6), were dissolved 1 g of copper chlorophyllin (product of Kanto Chemical Co., Inc.) and 1.5 mg of EDC (product of Dojindo Laboratories). The resultant solution was stirred for 3 days at room temperature by means of a magnetic stirrer. After the reaction mixture was dialyzed to deionized water through a dialysis membrane (molecular weight cut-off: 12K–14K) produced by Spectrum Company for 2 days, the dialyzate was lyophilized, thereby obtaining 1.13 g of dry powder.

The dry powder in an amount of 1.13 g was dissolved in chloroform to subject it to chromatography on a silica gel column (100 g) of 25 mm in diameter and 600 mm in length. As solvents, those having a composition of chloroform:methanol:acetic acid=100:0:1 to 60:40:1. The eluate was collected in 200-ml portions, and Fractions 13 to 14 were concentrated as Fraction B by a rotary evaporator and dialyzed under the same conditions as described above. The dialyzate was then lyophilized to obtain 67.3 mg of EDC-copper chlorophyllin(B). The product had an Rf value of 0.5 when conducting thin layer chromatography on silica gel (Merck) making use of a development solvent having a composition of chloroform:methanol:acetic acid=80:40:1

Preparation Example 10 (Synthesis of S-HSA-Hemin):

In 12.5 ml of 0.1N NaOH, were 30 mg of hemin powder, and the resultant solution was stirred for 5 minutes at room temperature. After 12.5 ml of distilled water were then added and the solution was stirred further for 5 minutes at room temperature, it was adjusted to pH 9.6 with acetic acid (referred to as Solution A). On the other hand, 450 mg of S-HSA were dissolved in a 20 ml of a solution obtained by adjusting 0.05N NaOH solution to pH 9.6 with acetic acid (referred to as Solution B). Solution B was added to Solution A, and the mixture was stirred for 2 hours at room temperature, and then dialyzed (molecular weight cut-off value: 12K–14K) to a 10 mM phosphate buffer (pH 7.3) for 2 days (4 liters×2) at 4° C., thereby obtaining 470 mg of S-HSA-Hemin.

Preparation Example 11 (Synthesis of S-HSA-EDC-Hemin):

(1) In 87 ml of 0.1N or 0.01N NaOH, were 870 mg of EDC-hemin powder, and the resultant solution was stirred for 5 minutes at room temperature. After 872 ml of distilled water were then added and the solution was stirred for 5 minutes at room temperature, 370 μl of acetic acid were added to adjust the solution to pH 9.6 (referred to as Solution A). On the other hand, 13,050 mg of S-HSA were dissolved in a 426 ml of a solution with 0.05N NaOH adjusted to pH 9.6 with acetic acid (referred to as Solution B). Solution B was added to Solution A, and the mixture was stirred for 2 hours at room temperature, and then dialyzed (molecular weight cut-off value: 12K–14K) to distilled water for 3 days (4 liters×3) at 4° C. The dialyzate was then lyophilized to obtain S-HSA-EDC-Hemin as powder.

(2) Under conditions of 4° C., 5 g of EDC-Hemin powder were added to 2.5 liters of 50 mM sodium citrate (pH 3). The mixture was stirred for 1 hour under conditions of shielding light (referred to as Solution A). On the other hand, 75 g of S-HSA were dissolved in 5 liters of 50 mM $NaHCO_3$ under conditions of 4° C. (referred to as Solution B).

While stirring Solution A under conditions of 4° C., Solution B was added at a rate of 5 ml/min. After the mixture was stirred for 2 hours under conditions of shielding light, it was dialyzed (molecular weight cut-off value: 12K–14K) to distilled water in a dark room at 4° C. The dialyzate was then lyophilized to obtain S-HSA-EDC-Hemin as powder.

Identification of S-HSA-Hemin and S-HSA-EDC-Hemin:

1. Cellulose acetate electrophoresis:

Each 1 μl of samples (S-HSA-Hemin, Hemin, S-HSA-EDC-Hemin, EDC-Hemin, S-HAS and HSA) was placed on a cellulose acetate membrane to conduct cellulose acetate electrophoresis by using 0.06M barbital buffer (pH 8.6) and applying an electric current of 8 mA.

Figure 26:
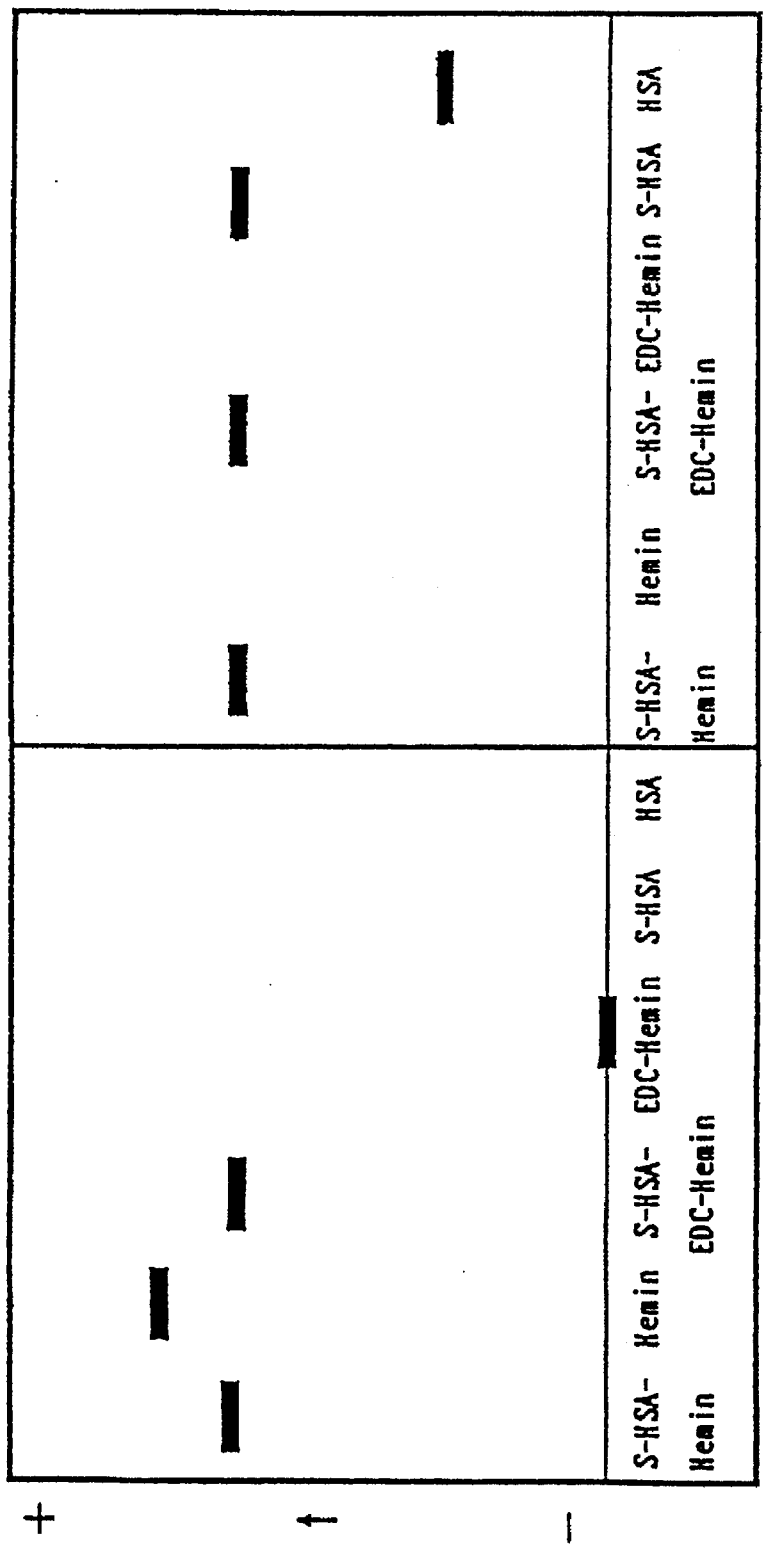
FIG. 26 illustrates electrophoresis of individual samples, of which the left-hand one shows an electropherogram of S-HSA-Hemin, Hemin, S-HSA-EDC-Hemin, EDC-Hemin, S-HSA and HSA after cellulose acetate electrophoresis but before protein staining, and the right-hand one shows an electrophoresis after protein staining.

The results are illustrated in FIG. 26. The left-hand one is an electrophoresis before protein staining, in which blackish brown bands attributable to hemin are shown. The right-hand one is an electrophoresis after protein staining making use of a Ponceau 3R stain (prepared by diluting 600 mg of Ponceau 3R and 6 g of trichloroacetic acid with water to 100 ml), which shows pink bands. From the comparison of both electrophoresis, it is apparent that with respect to S-HSA-EDC-Hemin and S-HSA-Hemin, the bands attributable to hemin consist with the bands attributable to the protein. Therefore, S-HSA-EDC-Hemin and S-HSA-Hemin are proved to migrate as they keep their complex form intact.

2. Gel filtration:

A sample was placed on a Sepharose CL6B column (product of Pharmacia AB, 15 mm in diameter×600 mm length), and elution was conducted by using 50 mM potassium phosphate buffer containing 0.2M NaCl at a flow rate of 0.5 ml/min, thereby measuring its spectrum. The results are illustrated in FIGS. 27 and 28.

Figure 27:
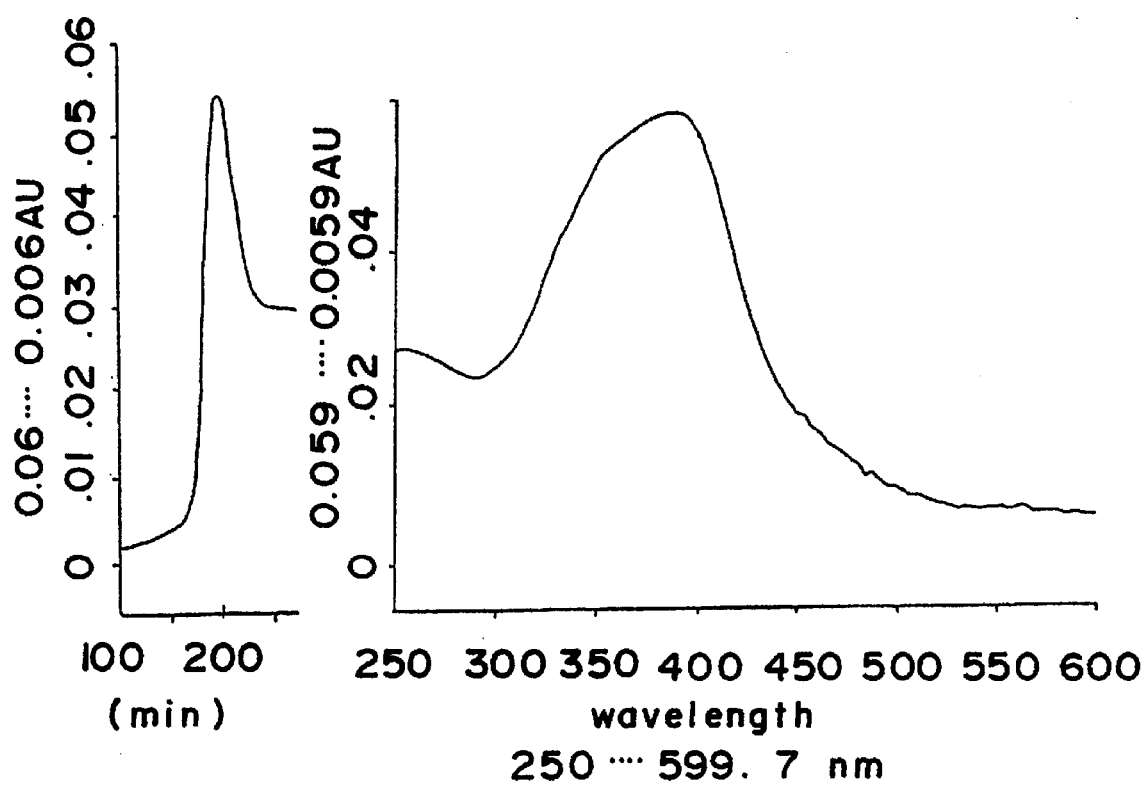
FIG. 27 illustrates the result of gel filtration as to EDC-Hemin, of which the left-hand one shows a gel filtration chromatogram of EDC-Hemin, and the right-hand one shows a spectrum of fractions eluted by the chromatography.
Figure 28:
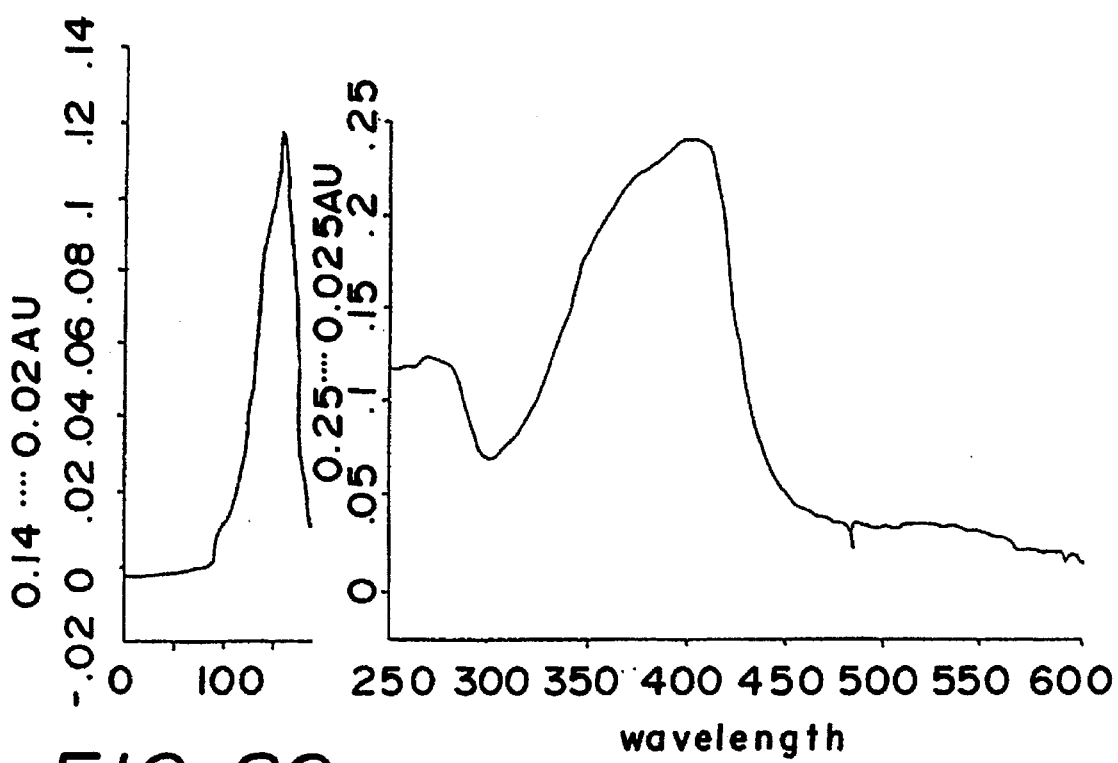
FIG. 28 illustrates the result of gel filtration as to S-HSA-EDC-Hemin, of which the left-hand one shows a gel filtration chromatogram of S-HSA-EDC-Hemin, and the right-hand one shows a spectrum of fractions eluted by the chromatography.

The left-hand one in FIG. 27 shows a chromatogram of EDC-Hemin at the absorbance of 400 nm. EDC-Hemin is eluted in 195 minutes. In the right-hand one showing a spectrum of this fraction, the absorption at 400 nm, which is attributed to Hemin, is indicated. The left-hand one in FIG. 28 shows a chromatogram of S-HSA-EDC-Hemin at the absorbance of 280 nm. As with EDC-Hemin, S-HSA-EDC-Hemin is eluted in 160 minutes. A spectrum of this fraction indicates absorption at both 280 nm attributable to the protein and 400 nm attributable to EDC-Hemin. This clearly proves that S-HSA and EDC-Hemin form a complex.

Preparation Example 12 (Synthesis of S-HSA-PP):

Thirty milligrams of PP powder were added to 2 ml of DMSO (product of Sigma Company), and the mixture was stirred for 2 hours at room temperature. Thereafter, 4 ml of distilled water were added and the mixture was stirred further for 1 hour at room temperature, thereby preparing Solution A.

On the other hand, 450 mg of S-HSA were dissolved in 6 ml of distilled water (pH turned to 5.28), thereby preparing Solution B.

Solution B was added to Solution A, and the mixture was stirred for 1 hour at room temperature, and then dialyzed to a 10 mM phosphate buffer (pH 7.3) through a dialysis membrane (molecular weight cut-off value: 12K–14K) for 2 days at 4° C., thereby obtaining S-HSA-PP.

Preparation Example 13 (Synthesis of S-HSA-EDC-PP):

Thirty milligrams of EDC-PP powder were added to 2 ml of DMSO (product of Sigma Company), and the mixture was stirred for 2 hours at room temperature. Thereafter, 4 ml of distilled water were added and the mixture was stirred further for 1 hour at room temperature, thereby preparing Solution A.

On the other hand, 450 mg of S-HSA were dissolved in 6 ml of distilled water (pH turned to 5.28), thereby preparing Solution B.

Solution B was added to Solution A, and the mixture was stirred for 1 hour at room temperature, and then dialyzed to a 10 mM phosphate buffer (pH 7.3) through a dialysis membrane (molecular weight cut-off value: 12K–14K) for 2 days at 4° C., thereby obtaining S-HSA-EDC-PP.

Incidentally, S-HSA-EDC-PP(A) and S-HSA-EDC-PP(B) may also be synthesized in the same procedure as described above.

Identification of S-HSA-PP, S-HSA-EDC-PP, S-HSA-EDC-PP(A) AND S-HAS-EDC-PP(B) by cellulose acetate electrophoresis:

Each 1 μl of samples (S-HSA-PP, S-HSA-EDC-PP, S-HSA-EDC-PP(A), S-HAS-EDC-PP(B), HSA and EDC-PP(A)+(B)) was placed on a cellulose acetate membrane to conduct cellulose acetate electrophoresis by using 0.06M barbital buffer (pH 8.6) and applying an electric current of 10 mA.

Figure 29:
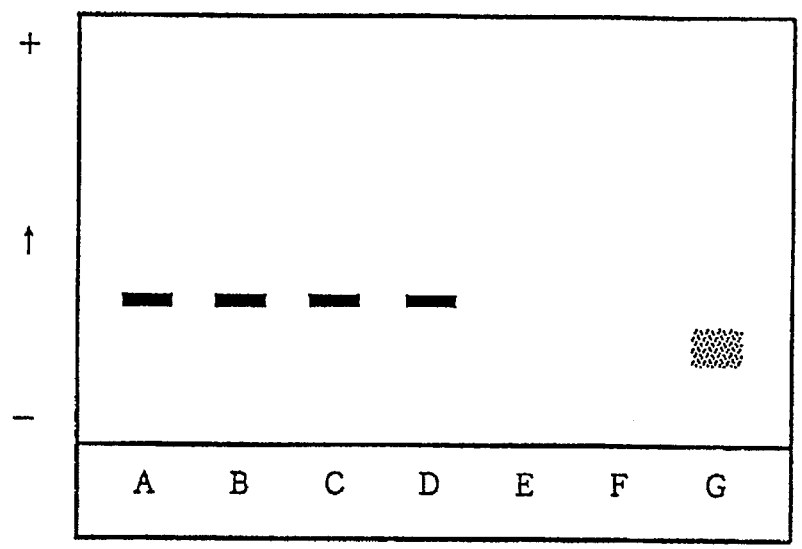
FIG. 29 illustrates electrophoresis of individual samples, of which the upper one shows an electrophoresis of S-HSA-PP, S-HSA-EDC-PP, S-HSA-EDC-PP(A), S-HSA-EDC-PP (B), S-HSA, HSA and EDC-PP(A)+(B) after cellulose acetate electrophoresis but before protein staining, and the lower one shows an electrophoresis after protein staining.
Figure 29:
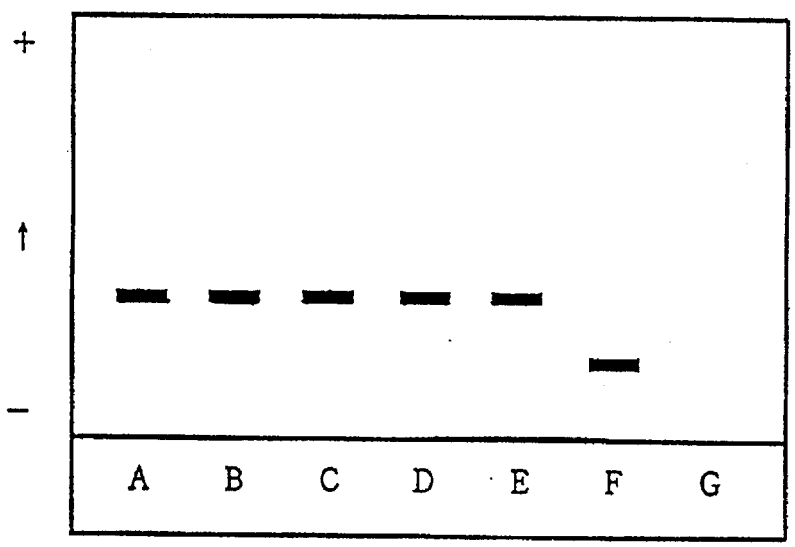

The results are illustrated in FIG. 29. The upper one is an electropherogram before protein staining, in which blackish brown bands attributable to PP are shown. The lower one is an electropherogram after protein staining making use of a Ponceau 3R stain (prepared by diluting 600 mg of Ponceau 3R and 6 g of trichloroacetic acid with water to 100 ml), which shows pink bands. From the comparison of both electropherograms, it is apparent that with respect to S-HSA-PP, S-HSA-EDC-PP, S-HSA-EDC-PP(A) AND S-HAS-EDC-PP(B), the bands attributable to PP consist with the bands attributable to the protein. Therefore, these compounds are proved to migrate as they keep their complex form intact.

Preparation Example 14:

S-HSA was reacted with various porphyrins in accordance with Preparation Examples 10–13 to prepare the following complexes.

HSA-EDC-Hemin
S-HSA-2EDC-Hemin
S-HSA-EDC-Fe-MesoP
S-HSA-CDC-Hemin(A)
S-HSA-CDC-Hemin(B)
S-HSA-IDC-Hemin
S-HSA-DMEA-Hemin
S-HSA-PEG-Hemin
S-HSA-EDC-copper chlorophyllin (B).

Test Example 1: Killing effect

The cell killing effects of test substances were determined using a cell strain persistently infected with HIV in MOLT-4 cells and MOLT-4 cells.

<Test substance>

The test substances are as follows. AZT, Hemin and S-HSA were used as references.

EDC-Hemin
EDC-PP
S-HSA-EDC-Hemin
S-HSA-EDC-PP
S-HSA-EDC-PP (A)
S-HSA-EDC-PP(B)
S-HSA-PP
AZT
Hemin
S-HSA <Method>

MOLT4/HTLV-III$_B$, MOLT4/ARV and MOLT4 cell strains were separately inoculated in proportions of $4\times10^4$ cells/well (200 μl) on a 96-well plate, and the above test substances in various concentrations were separately added in an amount of 20 μl thereto. After each cell sample was cultured for 3 days at 37° C. in the presence of 5% $CO_2$, the culture was diluted to a triple or quadruple amount, thereby counting the number of living cells by a trypan blue dye exclusion test. As a control, 20 μl of PBS were added in place of each test substance. The results of the test are shown in Table 1. Each numerical value is expressed in terms of the percentage of living cells to the control.

TABLE 1

|  | Conc. (μg/ml) | MOLT-4/HTLV-III$_B$ | MOLT-4/ARV | MOLT-4 |
| --- | --- | --- | --- | --- |
| EDC-Hemin | 1.2 | 3 |  | 0 |
|  | 0.6 | 67 |  | 44 |
|  | 0.3 | 91 |  | 92 |
| EDC—PP | 4.6 | 0 |  |  |
|  | 2.3 | 23 | 0 |  |
|  | 1.2 | 74 | 0 |  |
| S—HSA—EDC-Hemin | 151.6 | 0 | 0 |  |
|  | 113.7 | 0 |  | 2 |
|  | 75.8 | 28 | 61 | 45 |
|  | 37.9 | 69 | 72 | 104 |
| S—HSA—EDC—PP | 112.3 | 0 | 0 |  |

TABLE 1-continued

| | Conc. (μg/ml) | MOLT-4/HTLV-III$_B$ | MOLT-4/ARV | MOLT-4 |
|---|---|---|---|---|
| | 56.2 | 28 | 1 | |
| | 28.1 | 72 | 34 | |
| S—HSA—EDC—PP(A) | 679.2 | 0 | | |
| | 339.6 | 38 | 0 | |
| | 169.8 | 74 | 0 | |
| | 84.9 | 84 | 34 | |
| S—HSA—EDC—PP(B) | 1043.6 | 12 | | |
| | 521.8 | 39 | | |
| | 260.9 | 68 | 0 | |
| | 130.5 | 77 | 0 | |
| | 65.2 | 77 | 2 | |
| S—HSA—PP | 113.8 | 0 | 0 | |
| | 56.9 | 8 | 10 | |
| | 28.5 | 25 | 26 | |
| | 14.2 | 69 | 56 | |
| AZT | 1 μM | 71 | 82 | 55 |
| Hemin | 10 μM | 100 | 94 | 98 |
| | 40 μM | 90 | 93 | 99 |
| S—HSA | 100 | 100 | 100 | 100 |
| | (200 μg/ml) | | | |

Test Example 2: Killing effect and cytotoxic effect

The killing effect and cytotoxic effect of a test substance were determined using human peripheral blood lymphocytes and MOLT-4 cells.

<Test substance>

S-HSA-EDC-Hemin

<Method>

(1) Human peripheral blood lymphocyte:

Human peripheral blood lymphocytes (PBL) were separated by a Ficol. Part of them were activated and the remainder was used without activation. The activation of PBL was conducted by culturing PBL ($7 \times 10^5$/ml/10 ml) for 4 days in the presence of IL-2 and phytohaemagglutinin (PHA) in a 25-cm$^2$ culture flask. After the activated PBL was adjusted to $4 \times 10^5$/ml/10 ml and placed in a 25-cm$^2$ culture flask, 0.5 ml of the specimen solution was given in such a manner that the final concentration of S-HSA-EDC-Hemin reached a predetermined concentration, thereby culturing the cells for 24 hours. Thereafter, S-HSA-EDC-Hemin was removed, and the cells were cultured further for 2 days to count the number of living cells by the Trypan Blue dye exclusion method. With respect to the nonactivated PBL, PBL separated by Ficol was cultured for 4 days in the presence of S-HSA-EDC-Hemin in the various concentrations to count the number of living cells.

(2) MOLT-4 cells:

After MOLT-4/HTLV-III$_B$ cells and MOLT-4 cells were dosed with S-HSA-EDC-Hemin in various concentrations and cultured for 24 hours, S-HSA-EDC-Hemin was removed, and the cells were cultured further for 2 days to count the number of living cells. The results are shown in Table 2.

TABLE 2

| Control | Conc. (μg/ml) | PBL Activated 100 (%) | PBL Nonactivated 100 (%) | MOLT-4/HTLV-III$_B$ 100 (%) | MOLT-4 100 (%) |
|---|---|---|---|---|---|
| S—HSA—EDC-Hemin | 606.4 | | 22 | 0 | 0 |
| | 303.2 | 29 | 54 | 0 | 0 |
| | 227.4 | 77 | | | |
| | 151.6 | 81 | 70 | 0 | 0 |
| | 75.8 | 91 | 70 | 3 | 6 |
| | 37.9 | 88 | 98 | | |

Test Example 3: Killing effect and cytotoxic effect

The killing effects and cytotoxic effects of test substances were determined using MOLT-4/HTLV-III$_B$ cells, human peripheral blood lymphocytes (PBL) and human fibroblasts (IMR-90 and WI-38).

<Test substance>

EDC-Hemin
2EDC-Hemin
IDC-Hemin
HSA-EDC-Hemin
S-HSA-2EDC-Hemin
S-HSA-CDC-Hemin(A)
S-HSA-CDC-Hemin(B)
S-HSA-IDC-Hemin
S-HSA-EDC-Fe-MesoP
S-HSA-DMEA-Hemin
S-HSA-PEG-Hemin <Method>

(1) MOLT4/HTLV-III$_B$ cell:

MOLT4/HTLV-III$_B$ cells in a logarithmic growth phase were inoculated on a 96-well flat-bottom plate in a proportion of $2 \times 10^4$ cells/well (50 μl), and the above test substances in various concentrations were separately added in an amount of 50 μl thereto. After each cell sample was cultured for 3 days at 37° C. in the presence of 5% $CO_2$, the number of living cells was counted by the MTT assay. More specifically, a 7.5 mg of MTT [3-(4,5-dimethylthiazol-2-yl)-2,5-diphenyl-2H-tetrazolium bromide]/ml phosphate buffer was added in a proportion of 20 μl/well to each well, thereby conducting reaction for 2 hours at 37° C. in the presence of 5% $CO_2$. Then, 150 μl of a lysis solution [10% Triton X-100 solution in acid isopropanol] were added, and the mixture was thoroughly pipetted to solubilize the cells. Thereafter, the absorbance of the solution was measured.

(2) Human peripheral blood lymphocyte (PBL):

The test was conducted in substantially the same manner as in Test Example 2 except that the concentration of phytohaemagglutinin was changed to 3 μg/ml.

(3) Fibroblast:

Fibroblasts (IMR-90 or WI-38) in a logarithmic growth phase were inoculated on a 96-well microplate in a proportion of 50 μl per well ($0.2 \times 10^4$ cells), and the above test substances in various concentrations were separately added in a proportion of 50 μl/well thereto, thereby conducting culture at 37° C. in the presence of 5% $CO_2$. A culture medium was added in an amount of 50 μl to control wells. As the culture medium, there was used that obtained by adding, to RPMI-1640 (product of NIPPON SUISAN KAISHA, LTD.), 10% of fetal bovine serum, 100 μg/ml of penicillin, 100 μg/ml of streptomycin and 2 mM L-glutamine (all, products of GIBCO Laboratories) to its final concentration. The day the culture was started was defined as Day 0, and the time 5-day continuous culture was ended was defined as Day 5, whereby the number of living cells on Day 5 was counted by the above-described MTT assay.

The results thus obtained are shown in Tables 3, 4 and 5. Incidentally, the number of living cells was expressed in terms of % of the number of living cells in the control regarding the control as 100.

TABLE 3

| Test substance | Conc. (μg/ml) | MOLT-4/ HTLV-III$_B$ | Normal cell PBL | Fibroblast strain IMR-90 | WI-38 |
|---|---|---|---|---|---|
| EDC-Hemin | 2.4 | | 43 | 79 | 37 |
| | 1.2 | 0 | 65 | 73 | 50 |
| | 0.6 | 30 | 72 | 80 | 62 |
| | 0.3 | 78 | | 87 | 58 |
| 2EDC-Hemin | 125 | | | | |
| | 50 | 0 | 96 | | |
| | 25 | 0 | 87 | >100 | >100 |
| | 12.5 | 57 | | >100 | >100 |
| | 6.3 | 93 | | | |
| IDC-Hemin | 50 | | 24 | >100 | >100 |
| | 25 | 0 | 57 | >100 | >100 |
| | 12.5 | 0 | 75 | | |
| | 6.3 | 0 | >100 | | |
| | 3.2 | 65 | | | |

TABLE 4

| Test substance | Conc. (μg/ml) | MOLT-4/HTLV-III$_B$ | Normal cell PBL | Fibroblast strain IMR-90 | WI-38 |
|---|---|---|---|---|---|
| HSA—EDC-Hemin | 200 | 0 | | | |
| | 100 | 0 | | | |
| | 50 | 2 | | | |
| | 25 | 66 | | | |
| S—HAS—2EDC-Hemin | 500 | | 59 | 70 | 48 |
| | 400 | 0 | | | |
| | 250 | | >100 | 65 | 46 |
| | 200 | 30 | | | |
| | 125 | | >100 | 59 | 49 |
| | 100 | 100 | | | |
| S—HSA—CDC-Hemin(A) | 125 | | | 75 | 69 |
| | 50 | 0 | 88 | | |
| | 25 | 68 | | | |
| | 12.5 | 79 | | | |
| S—HSA—CDC-Hemin(B) | 200 | 0 | | | |
| | 100 | 33 | | | |
| | 50 | 61 | | | |
| | 25 | 69 | | | |
| S—HSA—IDC-Hemin | 125 | | | >100 | >100 |
| | 100 | 0 | 95 | | |
| | 50 | 0 | 92 | | |
| | 25 | 53 | 92 | | |

TABLE 5

| Test substance | Conc. (μg/ml) | MOLT-4/HTLV-III$_B$ | Normal cell PBL | Fibroblast strain IMR-90 | WI-38 |
|---|---|---|---|---|---|
| S—HSA—EDC—Fe—MesoP | 500 | | | 84 | 68 |
| | 200 | 0 | >100 | | |
| | 100 | 72 | >100 | | |
| | 50 | 86 | | | |
| S—HAS—DMEA-Hemin | 1000 | | 76 | >100 | >100 |
| | 500 | | >100 | >100 | >100 |
| | 400 | 0 | - | | |
| | 250 | 9 | >100 | | |
| | 200 | 23 | | | |
| | 100 | 90 | | | |
| S—HSA—PEG-Hemin | 1000 | | 53 | 79 | 71 |
| | 500 | | >100 | 81 | 74 |
| | 400 | 0 | | | |
| | 250 | 0 | >100 | 98 | 90 |
| | 200 | 26 | | | |
| | 100 | 88 | | | |
| S—HSA—EDC-copper chlorophyllin(B) | 250 | 0 | | | >100 |
| | 125 | 73 | | | >100 |
| | 63 | 81 | | | >100 |

Test Example 4: Killing effect on various HIV-infected cells

The killing effects of test substances on H9/MN cells, Hela/LAV cells and $_{OM}$-10.1 (HL-60/LAV) cells were determined in the same manner as in Test Example 3 (1). The results are shown in Table 6.

TABLE 6

| Test substance | Conc. (μg/ml) | H9/MN (use of $2 \times 10^4$ cell/well) | Hela/LAV (use of $0.8 \times 10^4$ cell/well) | OM-10.1 (use of $3 \times 10^4$ cell/well) |
|---|---|---|---|---|
| EDC-Hemin | 40 | | 0 | 0 |
| | 20 | | 2 | 8 |
| | 10 | | 43 | 58 |
| | 5 | | 59 | 90 |
| | 2.5 | | | 98 |
| S—HSA—EDC-Hemin | 400 | — | 2 | 4 |
| | 200 | 1 | 32 | 36 |
| | 100 | 3 | 72 | 78 |
| | 50 | 59 | 82 | 93 |
| | 25 | 79 | 91 | 98 |
| IDC-Hemin | 40 | | 0 | 12 |
| | 20 | 0 | 33 | 59 |
| | 10 | 19 | 62 | 90 |
| | 5 | 69 | 80 | 99 |
| | 2.5 | 89 | — | 102 |
| S—HSA—IDC-Hemin | 400 | | 0 | 2 |
| | 200 | | 32 | 23 |
| | 100 | | 68 | 71 |
| | 50 | | 80 | 101 |
| | 25 | | 90 | 107 |

Test Example 5: Anti-HIV effect

The inhibitory effects of test substances on the cytopathy and HIV antigen production of MT-4 cells due to HIV infection were determined.

<Test substances>

S-HSA-EDC-Hemin
S-HSA-Hemin
S-HSA
Hemin
AZT

<Method>

MT-4 cells belonging to a cell strain persistently infected with HTLV-1 are high in sensitivity to HIV and promptly die out when infected. MT-4/HIV cells which are MT-4 cells infected with HIV are used for screening anti-HIV agents making good use of this nature.

After MT-4 cells ($1.2 \times 10^7$ cells) were infected for 2 hours at 37° C. with 3.2 ml of HTLV-III$_B$ ($10^7$ TCID$_{50}$/ml) obtained from a culture supernatant of a cell strain persistently infected with HIV, i.e., MOLT-4/HOLV, the cells were washed. After the cells were then inoculated on a 48-well microplate in a proportion of $1 \times 10^5$ cells/well, the test substances were separately added in an amount of 100 μl. As a negative control, there was used a culture obtained by adding 3.2 ml of a culture supernatant after culturing MOLT-4 cells for 3 days to MT-4 cells ($4.7 \times 10^6$ cells), conducting culture for 2 hours at 37° C., washing the cells in the same manner as described above, inoculating them in a proportion of $1 \times 10^5$ cells/well and adding PBS in place of the test substances.

Upon elapsed time of 4 days after the culture, each supernatant was assayed on a P24gag protein based on an EIA kit produced by Abbott Labs, and the number of living cells was counted by the Trypan Blue dye exclusion method, and moreover, TCID$_{50}$ indicative of an actual quantity of infectious virus was calculated.

Figure 30:
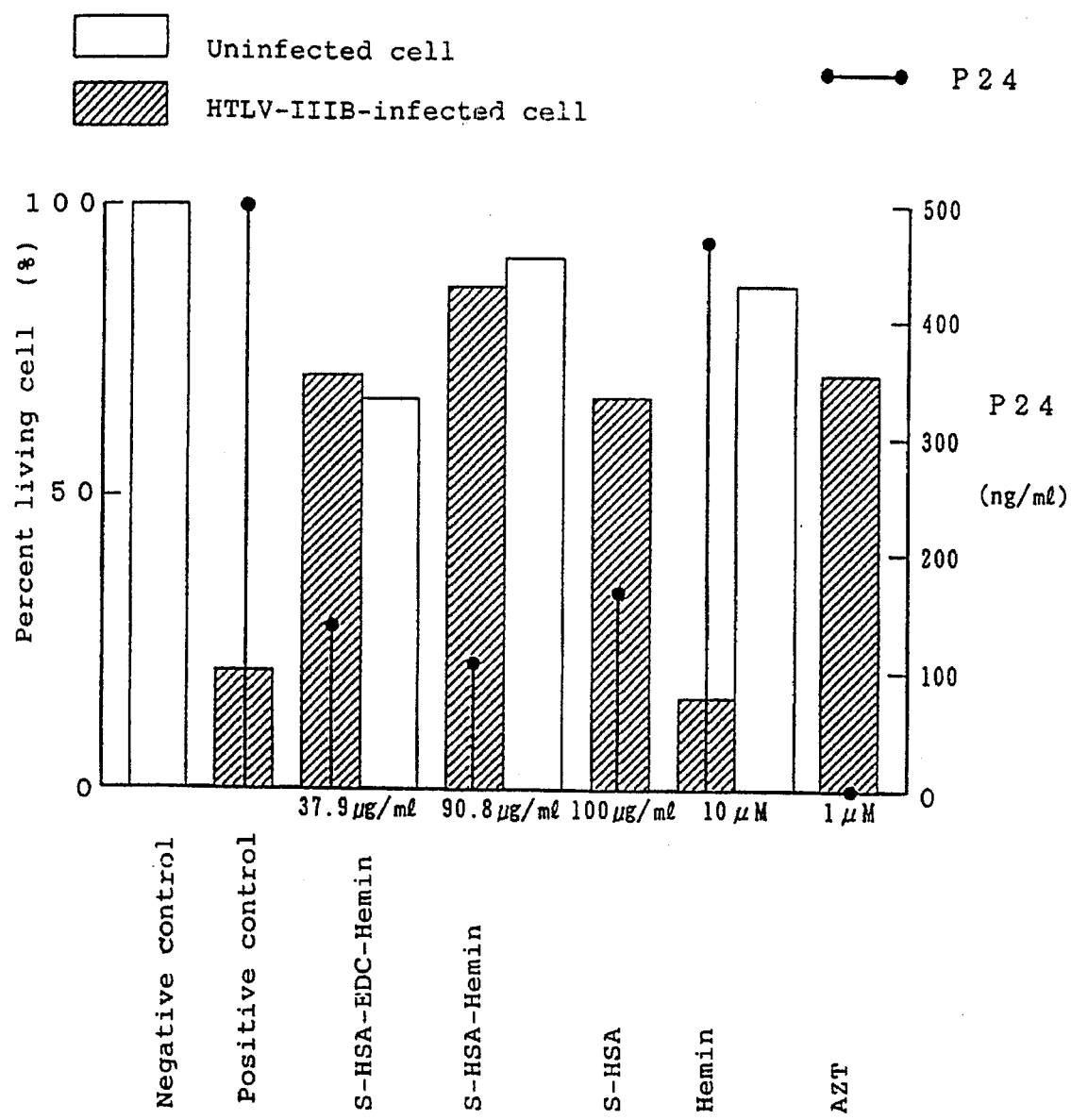
FIG. 30 illustrates the cytopathy inhibiting effect, P24 protein-production inhibiting effect and cytotoxic effect of S-HSA-EDC-Hemin, S-HSA-Hemin, S-HSA, Hemin and AZT on HTLV-III$_B$-infected cells and uninfected cells of MT-4 cells.

The results are shown in FIG. 30 and Table 7.

TABLE 7

| | Concentration | TCID$_{50}$/ml |
|---|---|---|
| Positive control | | $3.31 \times 10^7$ |
| S—HSA—EDC-Hemin | 37.9 μg/ml | $2.82 \times 10^4$ |
| S—HAS-Hemin | 90.8 μg/ml | $4.06 \times 10^3$ |
| S—HAS | 100 μg/ml | $1.64 \times 10^5$ |
| Hemin | 10 μM | $1.52 \times 10^7$ |
| AZT | 1 μM | $5.94 \times 10^4$ |

Test Example 6: Anti-HIV effect

The anti-HIV effects of test substances on human peripheral blood lymphocytes infected with HIV were determined.

<Test substances>

S-HSA-Hemin
S-HSA-EDC-Hemin

25

<Method>

After blood is collected from a vein by a syringe whose interior wall is wetted with heparin, PBL is separated from the blood with Ficol. After this PBL cell is inoculated on a 25-cm² culture flask containing 10 ml of a RPMI 1640 medium (including IL-2) added with 20% of a fetal bovine serum so as to contain $7 \times 10^5$ cells/ml therein, 40 µl (1 mg/ml) of PHA are added to culture the cells for 4 days. After 4 days, the cells are washed. Thereafter, they are used in assaying the anti-HIV effects of the test substances as PBL cells in an HIV-uninfected system for part of them, and in an HIV-infected system for the remainder. The PBL cells are inoculated on a 25-cm² culture flask added with 5 ml of the above medium so as to contain $2 \times 10^6$ cells therein. Then, 500 µl of S-HSA-Hemin or S-HSA-EDC-Hemin are given in various concentrations thereto so as to conduct culture at 37° C. in the presence of 5% $CO_2$, thereby assaying the cytotoxic effects of the test substances in the various concentrations. With respect to the infected system on the other hand, 8 ml of HTLV-III$_B$ ($10^7$ TCID$_{50}$/ml) obtained from a culture supernatant of an HIV-persistently infected strain, MOLT-4/HTLV-III$_B$ are inserted in the PBL cells to culture them for 2 hours. Thereafter, the cells are washed, and then inoculated on a 25-cm² culture flask added with 5 ml of the above medium so as to contain $2 \times 10^6$ cells therein. In the same manner as described above, S-HSA-Hemin or S-HSA-EDC-Hemin is given in the various concentrations thereto, thereby conducting culture at 37° C. in the presence of 5% $CO_2$. After 3, 6 and 9 days from the beginning of the culture, the number of cells are counted to calculate the quantity of the P24 protein produced and TCID$_{50}$. The results of the sixth day are shown in Table 8.

TABLE 8

|  | Concentration (µg/ml) | Living cells in uninfected system (%) | P24 production in infected system (%) |
|---|---|---|---|
| Control |  | 100 | 100 |
| S—HSA-Hemin | 181.6 | 66 | 1.7 |
|  | 90.8 | 88 | 3.1 |
|  | 45.4 | 113 | 4.8 |
| S—HSA—EDC-Hemin | 91.0 | 57 | 2.8 |
|  | 60.6 | 63 | 1.1 |
|  | 30.3 | 83 | 2.8 |
|  | 15.2 | 115 | 2.8 |

Test Example 7: Anti-HIV effect

The anti-HIV effects of test substances on human peripheral blood lymphocytes infected with HIV were determined.

<Test substances>

S-HSA-Hemin

S-HSA-EDC-Hemin

<Method>

After blood is collected from a vein by a syringe whose interior wall is wetted with heparin, PBL is separated from the blood with Ficol. After this PBL cell is inoculated on a 25-cm² culture flask containing 10 ml of a RPMI 1640 medium (including IL-2) added with 20% of a fetal bovine serum so as to contain $7 \times 10^5$ cells/ml therein, 40 µl (1 mg/ml) of PHA are added to culture the cells for 2 days. After 2 days, the cells are washed. Thereafter, they are used in assaying the anti-HIV effects of the test substances as PBL cells in an HIV-uninfected system for part of them, and in an HIV-infected system for the remainder. The PBL cells are inoculated on a 25-cm² culture flask added with 5 ml of the above medium so as to contain $2 \times 10^6$ cells therein. Then, 500 µl (final concentration: 200 µg/ml) of S-HSA-EDC-Hemin are given thereto so as to conduct culture at 37° C. in the presence of 5% $CO_2$, thereby assaying the cytotoxic effect of the test substance. With respect to the infected system on the other hand, 0.5 ml of HTLV-III$_B$ ($10^7$ TCID$_{50}$/ml) obtained from a culture supernatant of an HIV-persistently infected strain, MOLT-4/HTLV-III$_B$ is inserted in the PBL cells to culture them for 2 days. Thereafter, the cells are washed, and then inoculated on a 25-cm² culture flask added with 5 ml of the medium so as to contain $2 \times 10^6$ cells therein. In the same manner as described above, S-HSA-EDC-Hemin is given thereto, thereby conducting culture at 37° C. in the presence of 5% $CO_2$. After 4 days, the number of cells are counted to calculate the number of HIV envelope protein gp120 positive cells, analysis making use of FACS and the quantity of P24 protein produced.

<Result>

As shown in Table 9, in groups to which S-HSA-EDC-Hemin was given, the numbers of living cells in the uninfected system and the HIV-infected system after 4 days from the beginning of the culture are respectively 45% and 32% of the control (group given with no test substance).

On the other hand, the number of pg120 positive cells in the infected system was reduced to 16% compared with the day the test was started, while the number of cells increased 23-fold in the control group. From the above results, it was understood that S-HSA-EDC-Hemin has a cytotoxic effect, but exhibits a strong and specific killing effect on HIV-infected cells without being attended with the production of HIV.

TABLE 9

|  | Days of culture | 0 | 4 | Amount of S—HSA—EDC-Hemin (µg/ml) |
|---|---|---|---|---|
| Uninfected system | Total number of living cells ($\times 10^6$) | 2.0 | 19.1 | 0 |
|  |  | 2.0 | 8.6 | 200 |
| Infected system | Total number of living cells ($\times 10^6$) | 2.0 | 15.3 | 0 |
|  |  | 2.0 | 4.9 | 200 |
|  | Number of gp120 positive cells ($\times 10^6$) | 0.15 | 3.4 | 0 |
|  |  | 0.15 | 0.024 | 200 |
|  | Amount of p24 produced (ng/ml) | 70 | 279 | 0 |
|  |  | 70 | 8 | 200 |
|  |  | 70 | 8 | 200 |

Test Example 8: Inhibiting effect on formation of multinucleated giant cells (1) The inhibiting effects of test substances on the formation of multinucleated giant cells in a mixed culture system of Molt-4/C18 cells and Molt-4/III$_B$ cells were investigated.

Molt-4/C18 cells in a logarithmic growth phase were inoculated in a proportion of $2.5 \times 10^4$ cells/well (25 µl) on a 96-well flat-bottom plate. Similarly, Molt-4/HTL-VIII$_B$ cells in a logarithmic growth phase were inoculated in a proportion of $0.5 \times 10^4$ cells/well (25 µl) on the same plate. Then, solutions of the test substances in various concentrations were separately added in an amount of 50 µl, followed by their culture at 37° C. under conditions of 5% $CO_2$. To wells for a positive control, 50 µl of a culture medium were added in place of the solution of each test substance. To wells for a negative control, $3 \times 10^4$ cells/well (50 µl) of Molt-4/C18 cells and 50 µl of the culture medium instead of the solution of each test substance were added. Defining the day the culture was started as Day 0, the culture was continuously conducted for 3 days to observe a state of formation of multinucleated giant cells on Day 3 through a microscope. The state of formation of multinucleated giant cells was evaluated by scoring by 6 ranks with the negative control and the positive control ranked as (−) and (+++++), respectively. The results are shown in Table 10.

Incidentally, the composition of the culture medium is as follows:

RPMI-1640 (NIPPON SUISAN KAISHA, LTD.), fetal bovine serum (filtered, final concentration: 10%), penicillin-streptomycin (product of GIBCO Laboratories, penicillin final concentration: 100 units/ml+streptomycin final concentration: 100 µg/ml) and L-glutamine (product of GIBCO Laboratories, final concentration: 2 mM).

TABLE 10

|  | Concentration (µg/ml) | Score of formation multinucleated giant cells |
|---|---|---|
| Negative control | — | − |
| Positive control | — | +++++ |
| S—HSA—EDC-Hemin | 25 | − |
| S—HSA—EDC-Hemin | 12.5 | + |
| S—HSA—EDC-Hemin | 6.25 | ++ |
| S—HSA—EDC-Hemin | 3.125 | +++ |
| S—HSA—IDC-Hemin | 25 | + |
| S—HSA—IDC-Hemin | 12.5 | ++ |
| S—HSA—IDC-Hemin | 6.25 | ++ |
| S—HSA—IDC-Hemin | 3.125 | +++ |
| AZT | 25 (µM) | ++ |
| AZT | 0.5 | +++ |
| AZT | 0.1 | ++++ |
| AZT | 0.02 | +++++ |
| AZT | 0.004 | +++++ |

(2) The inhibiting effects of test substances on the formation of multinucleated giant cells and on cytopathy in a Molt-4/C18 cell-infected system were investigated.

Molt-4/C18 cells in a logarithmic growth phase were inoculated in a proportion of 2×10⁴ cells/well (20 µl) on a 96-well flat-bottom plate, and 30 µl of a culture supernatant of Molt-4/HTLV-III$_B$ cells were added. Then, solutions of the test substances in various concentrations were separately added in an amount of 50 µl, followed by their culture at 37° C. under conditions of 5% $CO_2$. To wells for a positive control, 50 µl of a culture medium were added in place of the solution of each test substance, while to wells for a negative control, 30 µl of the culture medium were added instead of the culture supernatant. Defining the day the culture was started as Day 0, the culture was continuously conducted for 4 days to observe a state of formation of multinucleated giant cells and to count the number of living cells by the MTT assay. The results are shown in Table 11.

TABLE 11

|  | Concentration (µg/ml) | Score of formation multinucleated giant cells | Number of living cells (%) |
|---|---|---|---|
| Negative control | — | − | 100 |
| Positive control | — | ++++ | 27 |
| S—HSA—EDC-Hemin | 25 | − | 45 |
| S—HSA—EDC-Hemin | 12.5 | − | 53 |
| S—HSA—EDC-Hemin | 6.25 | − | 71 |
| S—HSA—EDC-Hemin | 3.125 | + | 86 |
| S—HSA—IDC-Hemin | 25 | − | 48 |
| S—HSA—IDC-Hemin | 12.5 | − | 62 |
| S—HSA—IDC-Hemin | 6.25 | − | 82 |

TABLE 11-continued

|  | Concentration (µg/ml) | Score of formation multinucleated giant cells | Number of living cells (%) |
|---|---|---|---|
| S—HSA—IDC-Hemin | 3.125 | ± | 90 |
| AZT | 25 (µM) | + | 84 |
| AZT | 0.5 | ++ | 84 |
| AZT | 0.1 | +++ | 79 |
| AZT | 0.02 | ++++ | 69 |
| AZT | 0.004 | +++++ | 42 |

From the results of the above (1) and (2), it was proved that S-HSA-EDC-Hemin and S-HSA-IDC-Hemin each have an effect of inhibiting the adsorption and infection of HIV in the mixed culture system and cell-free system.

Test Example 9: One-administration toxicity test
(1) Intravenous-administration toxicity test:

A specimen was dissolved at a protein concentration of 100 mg/ml in a physiological saline (pH 7.0), and the solution was sterilely filtered through a membrane filter of 0.22 µm. The filtrate was intravenously administered to male ICR mice (Charles River Japan, Inc.) aged 5 weeks and 5 days through their tail veins. Doses of 690, 830, 1,000, 1,200 and 1,440 mg/kg were used in each group consisting of 5 mice. Defining the day of the administration as 0 day, their weights were measured on the second, fourth, seventh, tenth and fifteenth days. As a control, a group consisting of 5 mice given with no specimen was used.

(2) Intraperitoneal-administration toxicity test:

A specimen was dissolved at a protein concentration of 100 mg/ml in a physiological saline (pH 7.0), and the solution was sterilely filtered through a membrane filter of 0.22 µm. The filtrate was intraperitoneally administered to male ICR mice (Charles River Japan, Inc.) aged 5 weeks and 5 days. Defining the day of the administration as 0 day, their weights were measured on the second, fourth, seventh, tenth and fifteenth days.

(3) Oral-administration toxicity test:

A specimen was suspended in distilled water for injection to give a concentration of 50 mg/ml to orally administer (2,000 mg/kg) to 5 groups each consisting of 5 mice by a probe. Defining the day of the administration as 0 day, their weights were measured on the second, fourth, seventh, tenth and fifteenth days.

In each of the toxicity tests, organ autopsy was conducted to all the mice on the fifteenth day after the administration. The results are shown in Table 12 and FIG. 31.

TABLE 12

| Test substance | Route of administration | Dose (mg/kg) | Morality (Number of mice died/number of mice used) |
|---|---|---|---|
| S—HSA—EDC-Hemin | Intravenous | 1,440 | 1/5 |
|  |  | 1,200 | 0/5 |
|  |  | 1,000 | 0/5 |
|  |  | 830 | 0/5 |
|  |  | 690 | 0/5 |
| IDC-Hemin | Intravenous | 20 | 0/5 |
| S—HSA—IDC-Hemin | Intravenous | 400 | 0/5 |
| S—HSA—IDC-Hemin | Intraperitoneal | 400 | 0/5 |
| EDC-Hemin | Oral | 2,000 | 0/5 |

Figure 31:
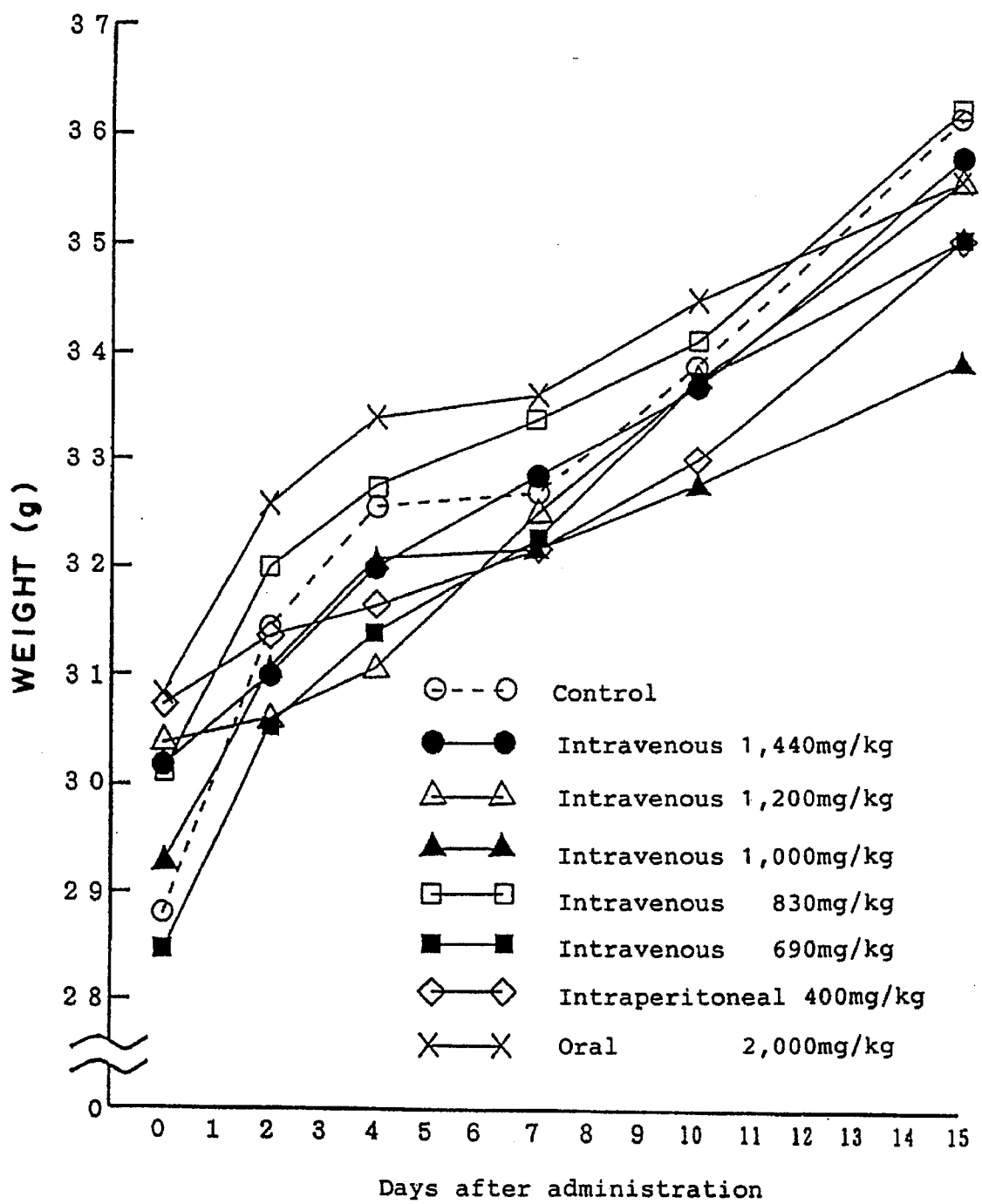

As apparent from the results of Table 12 and FIG. 31, S-HSA-EDC-Hemin showed no toxicity at doses of 1,200 mg/kg or less for the intravenous administration, 400 mg/kg or less for the intraperitoneal administration and 2,000 mg/kg or less for the oral administration. No abnormality was also recognized in changes in weight. Besides, with respect to S-HSA-IDC-Hemin, no deaths were recognized by the intravenous administration at a dose of 400 mg/kg or less.

As a result that the organ autopsy was conducted to all the mice on the fifteenth day, no abnormality was recognized in the intravenous and oral administration. However, intestinal adhesion, hepatomegaly and the like were recognized in the intraperitoneal administration of S-HSA-EDC-Hemin.

Test Example 10: Repeated-administration toxicity test

S-HSA-EDC-Hemin was repeatedly administered for 2 weeks at doses of 80, 200 and 500 mg/kg/day in veins of male ICR mice (Charles River Japan, Inc., 15 mice per group) to observe its effects.

As a result, transient piloerection, reduction in ultromotivity and pronation were found here and there in each dose group on the seventh to ninth day after starting the administration. However, no deaths were recognized in all the groups throughout the administration period.

From the results of Test Examples 1–10, it has been proved that the porphyrin derivatives (A) and (B) each have an effect of strongly killing HIV-infected cells, an HIV-infection inhibiting effect and an HIV-proliferation inhibiting effect in combination, and are extremely low in cytotoxic effect on human normal lymphocytes and toxicity. They are hence useful as novel anti-HIV agents having an action mechanism different from the conventional agents.

INDUSTRIAL APPLICABILITY

The anti-HIV agents according to the present invention are excellent in killing effect on HIV-infected cells, inhibitory effect on cytopathy due to HIV infection and HIV-replication inhibiting effect, and high in safety. They are hence useful as agents for the prophylaxis and treatment of AIDS.

We claim:

1. A method of killing HIV-infected cells in vitro which comprises administering an effective amount of a porphyrin derivative to HIV-infected cells in vitro, wherein said porphyrin derivative is the reaction product of a porphyrin compound and a carbodiimide compound; said porphyrin compound having a carboxyl terminated side chain at the 13 or 17 positions of said porphyrin compound, said carboxyl group including a carbonyl carbon atom; and said carbodiimide compound having a carbon atom double bonded to two nitrogen atoms which are reactable with said carboxyl group whereby said nitrogen atom of said carbodiimide compound is chemically bonded to said porphyrin compound via a chemical bond between said nitrogen atom and carbonyl carbon atom.

2. The method as claimed in claim 1, wherein the porphyrin is a compound selected from the group consisting of hemin, protoporphyrin, mesoporphyrin, iron mesoporphyrin, hematoporphyrin, iron hematoporphyrin, deuteroporphyrin, copper chlorophyllin and a physiologically acceptable salt of said porphyrin.

3. The method as claimed in claim 1, wherein the carbodiimide is a compound selected from the group consisting of N,N'-dicyclohexylcarbodiimide (DCC), 1-ethyl-3-(3-dimethylaminopropyl)carbodiimide (EDC), 1-cyclohexyl-3-(3-dimethylaminopropyl)carbodiimide (CDC), 1-isopropyl-3-(3-dimethylaminopropyl)-carbodiimide (IDC), and 1-cyclohexyl-3-(2-morpholinoethyl)carbodiimide (CMC).

4. The method as claimed in claim 1, wherein the porphyrin is a hemin and the carbodiimide is 1-ethyl-3-(3-dimethylaminopropyl)carbodiimide.

5. A method of killing HIV-infected cells in vitro which comprises administering an effective amount of a complex of a plasma protein or a chemically modified plasma protein and a porphyrin derivative to HIV-infected cells in vitro, wherein said chemically modified plasma protein is a protein obtained by a modification whereby polarity of the amino acid side chain is made negative(−), and said porphyrin derivative is the reaction product of a porphyrin compound and a carbodiimide compound; said porphyrin compound having a carboxyl terminated side chain at the 13 or 17 positions of said porphyrin compound, said carboxyl group including a carbonyl carbon atom; and said carbodiimide compound having a carbon atom double bonded to two nitrogen atoms which are reactable with said carboxyl group whereby said nitrogen atom of said carbodiimide compound is chemically bonded to said porphyrin compound via a chemical bond between said nitrogen atom and carbonyl carbon atom.

6. The method claimed in claim 5, wherein the plasma protein is a protein selected from the group consisting of human serum albumin, human immunoglobulin, human transferrin, human fibrinogen and bovine serum albumin.

7. The method claimed in claim 5, wherein the chemically modified plasma protein is a succinylated or maleylated plasma protein.

8. The method as claimed in claim 5, wherein the porphyrin is a compound selected from the group consisting of hemin, protoporphyrin, mesoporphyrin, iron mesoporphyrin, hematoporphyrin, iron hematoporphyrin, deuteroporphyrin, copper chlorophyllin and a physiologically acceptable salt of said porphyrin.

9. The method as claimed in claim 5, wherein the carbodiimide is a compound selected from the group consisting of N,N'-dicyclohexylcarbodiimide (DCC), 1-ethyl-3-(3-dimethylaminopropyl)carbodiimide (EDC), 1-cyclohexyl-3-(3-dimethylaminopropyl)carbodiimide (CDC), 1-isopropyl-3-(3-dimethylaminopropyl)-carbodiimide (IDC), and 1-cyclohexyl-3-(2-morpholinoethyl)carbodiimide (CMC).

10. The method claimed in claim 5, wherein the chemically modified plasma protein is a succinylated human serum albumin, the porphyrin is a hemin, and the carbodiimide is 1-ethyl-3-(3-dimethylaminopropyl)carbodiimide.

11. The method as claimed in claim 5, wherein the porphyrin compound is S-HSA-EDC-Hemin, IDC-Hemin, S-HSA-IDC-Hemin, or EDC-Hemin.

12. A composition for killing HIV-infected cells which comprises an effective amount of a porphyrin derivative wherein said porphyrin derivative is the reaction product of a porphyrin compound and a carbodiimide compound; said porphyrin compound having a carboxyl terminated side chain at the 13 or 17 positions of said porphyrin compound, said carboxyl group including a carbonyl carbon atom; and said carbodiimide compound having a carbon atom double bonded to two nitrogen atoms which are reactable with said carboxyl group whereby said nitrogen atom of said carbodiimide compound is chemically bonded to said porphyrin compound via a chemical bond between said nitrogen atom and carbonyl carbon atom.

13. The composition as claimed in claim 12, wherein the porphyrin is a compound selected from the group consisting of hemin, protoporphyrin, mesoporphyrin, iron mesoporphyrin, hematoporphyrin, iron hematoporphyrin, deuteroporphyrin, copper chlorophyllin and a physiologically acceptable salt of said porphyrin.

14. The composition as claimed in claim 12, wherein the carbodiimide is a compound selected from the group consisting of N,N'-dicyclohexylcarbodiimide (DCC),
1-ethyl-3-(3-dimethylaminopropyl)carbodiimide (EDC),
1-cyclohexyl-3-(3-dimethylaminopropyl)carbodiimide (CDC),
1-isopropyl-3-(3-dimethylaminopropyl)-carbodiimide (IDC), and
1-cyclohexyl-3-(2-morpholinoethyl)carbodiimide (CMC).

15. The composition claimed in claim 12, wherein the porphyrin is a hemin and the carbodiimide is 1-ethyl-3-(3-dimethylaminopropyl)carbodiimide.

16. A composition for killing HIV-infected cells which comprises a carrier and an effective amount of a complex of a plasma protein or a chemically modified plasma protein and a porphyrin derivative, wherein said chemically modified plasma protein is a protein obtained by a modification whereby polarity of the amino acid side chain is made negative(−), and said porphyrin derivative is the reaction product of a porphyrin compound and a carbodiimide compound; said porphyrin compound having a carboxyl terminated side chain at the 13 or 17 positions of said porphyrin compound, said carboxyl group including a carbonyl carbon atom; and said carbodiimide compound having a carbon atom double bonded to two nitrogen atoms which are reactable with said carboxyl group whereby said nitrogen atom of said carbodiimide compound is chemically bonded to said porphyrin compound via a chemical bond between said nitrogen atom and carbonyl carbon atom.

17. The composition claimed in claim 16, wherein the plasma protein is a protein selected from the group consisting of human serum albumin, human immunoglobulin, human transferrin, human fibrinogen and bovine serum albumin.

18. The composition claimed in claim 16, wherein the chemically modified plasma protein is a succinylated or maleylated plasma protein.

19. The composition as claimed in claim 16, wherein the porphyrin is a compound selected from the group consisting of hemin, protoporphyrin, mesoporphyrin, iron mesoporphyrin, hematoporphyrin, iron hematoporphyrin, deuteroporphyrin, copper chlorophyllin and a physiologically acceptable salt of said porphyrin.

20. The composition as claimed in claim 16, wherein the carbodiimide is a compound selected from the group consisting of N,N'-dicyclohexylcarbodiimide (DCC),
1-ethyl-3-(3-dimethylaminopropyl)carbodiimide (EDC),
1-cyclohexyl-3-(3-dimethylaminopropyl)carbodiimide (CDC),
1-isopropyl-3-(3-dimethylaminopropyl)-carbodiimide (IDC), and
1-cyclohexyl-3-(2-morpholinoethyl)carbodiimide (CMC).

21. The composition as claimed in claim 16, wherein the chemically modified plasma protein is a succinylated human serum albumin, the porphyrin is a hemin, and the carbodiimide is 1-ethyl-3-(3-dimethylaminopropyl)carbodiimide.

22. The composition as claimed in claim 16, wherein the porphyrin compound is S-HSA-EDC-Hemin, IDC-Hemin, S-HSA-IDC-Hemin, or EDC-Hemin.

23. The method of claim 1 wherein the porphyrin compound has a carboxyl terminated side chain at the 13 and 17 positions of said porphyrin compound.

24. The method of claim 5 wherein the porphyrin compound has a carboxyl terminated side chain at the 13 and 17 positions of said porphyrin compound.

25. The composition of claim 12 wherein the porphyrin compound has a carboxyl terminated side chain at the 13 and 17 positions of said porphyrin compound.

26. The composition of claim 16 wherein the porphyrin compound has a carboxyl terminated side at the 13 and 17 position of said porphyrin compound.

* * * * *